US010752664B2

(12) United States Patent
Xiong et al.

(10) Patent No.: US 10,752,664 B2
(45) Date of Patent: Aug. 25, 2020

(54) METHOD OF TREATING OR AMELIORATING METABOLIC DISORDERS USING GROWTH DIFFERENTIATION FACTOR 15 (GDF-15)

(75) Inventors: YuMei Xiong, San Bruno, CA (US); Yang Li, Mountain View, CA (US); Wen-Chen Yeh, Belmont, CA (US); Bei Shan, Redwood City, CA (US); Jackie Zeqi Sheng, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 424 days.

(21) Appl. No.: 14/009,790

(22) PCT Filed: Apr. 5, 2012

(86) PCT No.: PCT/US2012/032415
§ 371 (c)(1),
(2), (4) Date: Nov. 6, 2013

(87) PCT Pub. No.: WO2012/138919
PCT Pub. Date: Oct. 11, 2012

(65) Prior Publication Data
US 2015/0307575 A1    Oct. 29, 2015

Related U.S. Application Data

(60) Provisional application No. 61/473,583, filed on Apr. 8, 2011.

(51) Int. Cl.
| C07K 14/495 | (2006.01) |
| A61K 38/00 | (2006.01) |
| A61K 38/18 | (2006.01) |

(52) U.S. Cl.
CPC ............ *C07K 14/495* (2013.01); *A61K 38/18* (2013.01); *A61K 38/00* (2013.01)

(58) Field of Classification Search
None
See application file for complete search history.

(56) References Cited

U.S. PATENT DOCUMENTS

| 3,773,919 | A | 11/1973 | Du Pont |
| 6,737,056 | B1 | 5/2004 | Presta |
| 8,338,569 | B2 | 12/2012 | Marshall et al. |
| 8,362,210 | B2 | 1/2013 | Lazar et al. |
| 8,372,952 | B2 | 2/2013 | Smith et al. |
| 9,248,181 | B2 | 2/2016 | De Kruif |
| 9,272,019 | B2 | 3/2016 | Shaw et al. |
| 9,550,819 | B2 | 1/2017 | Lindhout |
| 9,714,276 | B2 | 7/2017 | Xiong et al. |
| 9,862,752 | B2 | 1/2018 | Xiong et al. |
| 10,195,250 | B2 | 2/2019 | Lindhout et al. |
| 10,336,812 | B2 | 7/2019 | Armstrong et al. |

| 2004/0053366 | A1 | 3/2004 | Lo et al. |
| 2006/0275283 | A1 | 12/2006 | Van Vlijmen et al. |
| 2007/0054853 | A1* | 3/2007 | Fujise .................... C07K 14/47 514/1.9 |
| 2009/0004181 | A1* | 1/2009 | Breit ....................... C07K 16/22 424/133.1 |
| 2010/0087627 | A1 | 4/2010 | Marshall et al. |
| 2010/0278843 | A1 | 11/2010 | Breit et al. |
| 2011/0150901 | A1 | 6/2011 | Smith et al. |
| 2011/0195067 | A1 | 8/2011 | Arnason et al. |
| 2011/0229472 | A1 | 9/2011 | Min et al. |
| 2011/0236375 | A1 | 9/2011 | Lazar et al. |
| 2013/0336981 | A1 | 12/2013 | De Kruif et al. |
| 2015/0023960 | A1 | 1/2015 | Lindhout et al. |
| 2015/0139996 | A1 | 5/2015 | De Kruif et al. |
| 2015/0307575 | A1 | 10/2015 | Xiong |
| 2016/0030585 | A1 | 2/2016 | Barnes et al. |
| 2017/0107248 | A1 | 4/2017 | Lou et al. |
| 2017/0204149 | A1 | 7/2017 | Chopra et al. |
| 2017/0291929 | A1 | 10/2017 | Xiong et al. |
| 2018/0079790 | A1 | 3/2018 | Xiong et al. |
| 2019/0000923 | A1 | 1/2019 | Chutkow et al. |
| 2019/0248852 | A1 | 8/2019 | Zhang et al. |
| 2019/0292241 | A1 | 9/2019 | Armstrong et al. |
| 2019/0309033 | A1 | 10/2019 | Gonciarz et al. |

FOREIGN PATENT DOCUMENTS

| CN | 1723220 A | 1/2006 |
| CN | 1974601 A | 6/2007 |
| EP | 0036676 B2 | 9/1981 |
| EP | 0036776 A2 | 9/1981 |
| EP | 0058481 A1 | 8/1982 |
| EP | 0088046 A2 | 9/1983 |
| EP | 0133988 A2 | 3/1985 |
| EP | 0143949 A1 | 6/1985 |

(Continued)

OTHER PUBLICATIONS

Johnen et al, Tumor-induced anorexia and weight loss are mediated by the TGF-b superfamily cytokine MIC-1 (Nat Med. Nov. 2007;13(11):1333-40).*
Diabetes self-management (downloaded online from URL:< http://www.diabetesselfmanagement.com/diabetes-resources/definitions/prediabetes/>, 2006).*
Aronne, Treating Obesity: A New Target for Prevention of Coronary Heart Disease (Prog Cardiovasc Nurs. 2001;16(3)).*
Dinsmoor (downloaded online from URL:< http://www.diabetesselfmanagement.com/managing-diabetes/complications-prevention/protecting-your-kidneys/, 2009).*
GenBank: AF003934.1 (*Homo sapiens* prostate differentiation factor mRNA, complete cds, 1997).*

(Continued)

*Primary Examiner* — Sergio Coffa

(57) ABSTRACT

Methods of treating metabolic diseases and disorders using a GDF15 polypeptide are provided. In various embodiments the metabolic disease or disorder is type 2 diabetes, obesity, dyslipidemia, elevated glucose levels, elevated insulin levels and diabetic nephropathy.

11 Claims, 18 Drawing Sheets

Specification includes a Sequence Listing.

(56) References Cited

FOREIGN PATENT DOCUMENTS

| | | |
|---|---|---|
| EP | 2330197 A2 | 6/2011 |
| EP | 2 439 535 | 4/2012 |
| EP | 2694092 B1 | 1/2017 |
| JP | 2003-081831 A | 3/2003 |
| JP | 2007-532586 A | 11/2007 |
| JP | 2010-536717 A | 12/2010 |
| WO | 1993/15722 A1 | 8/1993 |
| WO | 1999/06445 A1 | 2/1999 |
| WO | 2005/077981 A2 | 8/2005 |
| WO | 2005/099746 | 10/2005 |
| WO | 2006/000448 A2 | 1/2006 |
| WO | 2007/041635 A2 | 4/2007 |
| WO | 2009/021293 | 2/2009 |
| WO | 2009089004 A1 | 7/2009 |
| WO | WO 2009/141357 | 11/2009 |
| WO | 2010017198 A2 | 2/2010 |
| WO | 2010/048670 A1 | 5/2010 |
| WO | 2011063348 A1 | 5/2011 |
| WO | 2011/064758 A2 | 6/2011 |
| WO | 2012007868 A2 | 1/2012 |
| WO | 2012007869 A2 | 1/2012 |
| WO | 2012007877 A2 | 1/2012 |
| WO | WO 2012/025355 | 3/2012 |
| WO | 2012058768 A1 | 5/2012 |
| WO | 2012125850 A1 | 9/2012 |
| WO | 2012/138919 A1 | 10/2012 |
| WO | 2012146628 A1 | 11/2012 |
| WO | 2013/113008 A1 | 8/2013 |
| WO | 2013/148117 A1 | 10/2013 |
| WO | 2013157953 A1 | 10/2013 |
| WO | 2013157954 A1 | 10/2013 |
| WO | 2014/100689 A1 | 6/2014 |
| WO | 20170121865 A1 | 7/2017 |
| WO | 20170147742 A1 | 9/2017 |
| WO | 20170152105 A1 | 9/2017 |

OTHER PUBLICATIONS

Abma (Blood Sugar Monitoring: When to Check and Why, 2009).*
Biotek (Determination of Insulin Levels in Human Serum, 2009).*
Johnen et al (Nature Medicine 13, 1333-1340 (2007)).*
Inoue et al (Nat Med. Feb. 2004;10(2):1 68-74).*
Cekanova, et al. Nonsteroidal anti-inflammatory drug-activated gene-1 expression inhibits urethane-induced pulmonary tumorigenesis in transgenic mice. Cancer Prev Res (Phila). May 2009; 2(5):450-458.
Creative BioMart. Recombination Human Growth Differentiation Factor 15. Fc Chimera; Oct. 23, 2010 (according to document properties for posted document); (Retrieved from the Internet Apr. 9, 2013 <http://img.creativebiomart.net1pdf/GDF15-204H.GDF15,Fc%20Chimera.pdf>.
Czajkowsky, et al. Fc-fusion proteins: new developments and future perspectives. EMBO Mol Med.; Epub Jul. 26, 2012; 4(10):1015-1028.
Macia Laurence et al "Macrophage inhibitory cytokine 1 (MIC-1/GDF15) decreases food intake, body weight and improves glucose tolerance in mice on normal & obesogenic diets.", PLOS ONE, vol. 7, No. 4, E34868, 2012, pp. 1-8.
Dostálová Ivana et al: "Increased serum concentrations of macrophage inhibitory cytokine-1 in patients with obesity and type 2 diabetes mellitus: the influence of very low caloric diet.", European Journal of Endocrinology / European Federation of Endocrine Societies Sep. 2009, vol. 161, No. 3, (Sep. 2009), pp. 397-404.
Lind Lars et al: "Growth-differentiation factor-15 is an independent marker of cardiovascular dysfunction and disease in the elderly: results from the Prospective Investigation of the Vasculature in Uppsala Seniors (PIVUS) Study", European Heart Journal (Online), Oxford University Press, GB, US, NL, vol. 30, No. 19, Oct. 1, 2009 (Oct. 1, 2009), pp. 2346-2353.
Lajer Maria et al: "Plasma growth differentiation factor-15 independently predicts all-cause and cardiovascular mortality as well as deterioration of kidney function in type 1 diabetic patients with nephropaty.", Diabetes Care, vol. 33, No. 7, Jul. 2010 (Jul. 2010), pp. 1567-1572.
Johnen Heiko et al: "Tumor-induced anorexia and weight loss are mediated by the TGF-beta superfamily cytokine MIC-1", Nature Medicine, vol. 13, No. 11, Nov. 1, 2007 (Nov. 1, 2007), pp. 1333-1340.
Jensen, et al. A novel Fe gamma receptor ligand augments humoral responses by targeting antigen to Fe gamma receptors. Eur .. J. Immunol.; 2007; 37(4):1139-48.
Mekhaiel, et al. Polymeric human Fe-fusion proteins with modified effector functions. Sci Rep.; 2011; 1:124.
White et al.—Rapid Immune Responses to a Botulinum Neurotoxin Hc Subunit Vaccine through In Vivo Targeting to Antigen-Presenting Cells Infect. Immun.; Epub May 16, 2011;79(8): 3388-3396.
White, et al. Design and expression of polymeric immunoglobulin fusion proteins: a strategy for targeting low-affinity Fegamma receptors. Protein Expr; Purif.; 2001; 21(3):446-455.
NCBI Reference Sequence: NP 004855.2, 2015.
Beck et al., "Therapeutic Fc-fusion proteins and peptides as successful alternatives to antibodies", *MABS*, (2011) 3(5):415-416.
American Diabetes Association, "Standards of Medical Care in Diabetes," Diabetes Care, 33(1):S11-S61 (2011).
Ausubel et al., eds., Current Protocols in Molecular Biology, Green Publishers Inc. and Wiley and Sons, (1994) (Table of Contents Only).
Baek SJ, "Molecular Cloning and Characterization of Human Nonsteroidal Anti-Inflammatory Drug-activated Gene Promoter," *J. Biol Chemistry*, 276(36):33384-33392 (2001).
Baek SJ et al. "Nonsteroidal Anti-Inflammatory Drug-Activated Gene-1 Over Expression in Transgenic Mice Suppresses Intestinal Neoplasia" *Gastroenterology*, 131:1553-1560 (2006).
Bauskin AR et al., "The Propeptide of Macrophage Inhibitory cytokine (MIC-1), a TGF-β superfamily member, acts as a quality control determinant for correctly folded MIC-1," EMBO J., 19(10):2212-2220; (2000).
Beck & Reichert, MABS, 3(5):415-416 (2011).
Berge et al., "Pharmaceutical Salts", J. Pharm. Science, 1977, 6661, 1-19.
Bootcov MR, Proc Natl Acad Sci 94:11514-11519 (1997).
Bottner M ,Gene, 237:105-11 (1999).
Carrillo et al., SIAM J. Applied Math., 48:1073 (1988).
Dayhoff et al., Atlas of Protein Sequence and Structure, 5:345-352 (1978).
Devereux et al., Nucl. Acid Res., 12:387 (1984).
Eppstein et al., Proc. Natl. Acad. Sci. US, 82: 3688-3692 (1985).
Fairlie WD, Gene, 254: 67-76 (2000).
Freiberg & Zhu, Int. J. Pharm., 282:1-18 (2004).
Gribskov, M. and Devereux, J., eds., *Sequence Analysis Primer*, New York: M. Stockton Press (1991) (Table of Contents Only).
Griffin, A. M., and New Jersey: Humana Press Griffin, H. G., eds., *Computer Analysis of Sequence Data, Part I*, New Jersey: Humana Press (1994) (Table of Contents Only).
Gunasekaran K., et al. : "Enhancing Antibody 2-24 Fc Heterodimer Formation through Electrostatic Steering Effects: Applications to Bispecific Molecules and Monovalent IgG", Journal of Biological Chemistry, vol. 285, No. 25, Jun. 18, 2010 (2010-18), pp. 19637-19646.
Henikoff et al., Proc. Natl. Acad. Sci. USA, 89:10915-10919 (1992).
Hromas R. et al., Biochim Biophys Acta., 1354:40-44 (1997).
Katoh M, et al., Int J Mol Med, 17:951-955 (2006).
Kempf T, "The Transforming Differentiation Factor-{sligbeta} Superfamily Member Growth-Differentiation Factor-15 Protects the Heart From Ischemia/Reperfusion Injury", Circ Res., 98:351-360 (2006).
Langer et al., J. Biomed. Mater. Res., 15:267-277 (1981).
Langer, Chem. Tech., 12: 98-105 (1982).
Lawton LN, "Identification of a novel member of the TGF-beta superfamily highly expressed in human placenta", Gene, 203:17-26 (1997).

(56) References Cited

OTHER PUBLICATIONS

Moore A.G., "The transforming growth factor-ss superfamily cytokine macrophage inhibitory cytokine-1 is present in high concentrations in the serum of pregnant women", J Clin Endorcinol Metab, 85: 4781-4788 (2006).
Needleman et al., J. Mol. Biol., 48:443-453 (1970).
Paralkar VM, "Cloning and characterization of a novel member of the transforming growth factor-beta/bone morphogenetic protein family", J. Biol. Chemistry, 273:13760-13767 (1998).
Sambrook, J., Fritsh, E. F., and Maniatis, T. *Molecular Cloning: A Laboratory Manual* 2nd, ed., Cold Spring Harbor Laboratory, Cold Spring Harbor Laboratory Press, Cold Spring Harbor, N.Y., (1989) (Table of Contents Only).
Sidman et al., Biopolymers, 22: 547-56 (1983).
Smith, D. W., ed, *Biocomputing Informatics and Genome Projects*, New York: Academic Press (1993) (Table of Contents Only).
Strelau J, "Progressive Postnatal Motoneuron Loss in Mice Lacking GDF-15", J Neuroscience, 29:13640-13648 (2009).
Tamary H et al., "Elevated growth differentiation factor 15 expression in patients with congenital dyserythropoietic anemia type I," 112:5241-5244 (2008).
Tanno T, "High levels of GDF15 in thalassemia suppress expression of the iron regulatory protein hepcidin", Nat Med, 13:1096-1101 (2007).
Van Heeke & Schuster, "Expression of human asparagine synthetase in *Escherichia coli*", J. Biol. Chem., 264: 5503-5509 (1989).
Wilson and Gisvold, *Textbook of Organic Medicinal and Pharmaceutical Chemistry*, Delgado and Remers, Eds., 10th ed., Lippincott-Raven Publishers Philadelphia-New York (1998) (Table of Contents Only).
Wischke & Schwendeman, Int. J. Pharm., 364: 298-327 (2008).
Xu J, "GDF15/MIC-1 Functions As a Protective and Antihypertrophic Factor Released From the Myocardium in Association With SMAD Protein Activation", Circ Res., 98:342-350 (2006).
Zimmerman MB, "Iron metabolism in heterozygotes for hemoglobin E (HbE), -thalassemia 1, or -thalassemia and in compound heterozygotes for HbE/-thalassemia", Am J Clin Nutr, 88:1026-1031 (2008).
Alain et al., Therapeutic Fc-fusion proteins and peptides as successful alternatives to antibodies, MABS, 3:5, 415-416 (2011).
Ansel et al., Pharmaceutical Dosage Forms & Drug Delivery Systems, 7th ed. 2000.
Aulton, Pharmaceutics: the Science of Dosage Form Design, Churchill Livingstone, New York, 1988.
Computational Molecular Biology, Lesk, A.M., ed., 1988, New York: Oxford University Press; Biocomputing Informatics and Genome Projects, Smith, D. W., ed., 1993, New York: Academic Press.
Dayhoff et al., Atlas of Protein Sequence and Structure, 1978, 5:345-352.
Lo et al. (2005, Protein Engineering, Design & Selection 18:1-10).
Massague, J., "TGFβ in Cancer," Cell, 134, 215-230 (2008).
Remington: The Science and Practice of Pharmacy, 19th edition, 1995.

Rose-John et al., "The IL-6/sIL-6R complex as a novel target for therapeutic approaches," Expert Opinion on Therapeutic Targets, 11:5, 613-624 (2007).
Sino Biological Inc. (http://www.sinobiological.com/GDF-15-Protein-g-570.html; available May 1, 2010.
Von Heinje, G., Sequence Analysis in Molecular Biology, 1987, New York: Academic Press.
Brodkin et al., "Prediction of distal residue participation in enzyme catalysis," *Protein Science*, 24:762-778 (2015).
Butt et al., "Diabetic Nephropathy," Cleveland Clinic Center for Continuing Education (2010).
Coleman et al., "The Influence of Genetic Background on the Expression of the Obese (ob) Gene in the Mouse," *Diabetologia*, 9(4):287-293 (1973).
Dairman, T "Prediabetes,", *Diabetes Self-Management* (2006).
Dinsmoor, R. S., "Proteinuria," *Diabetes Self-Management* (2006).
Emmerson et al., "The metabolic effects of GDF15 are mediated by the orphan receptor GFRAL," *Nature Medicine*, 23(10):1215-1219 (2017).
Etzweiler, D., "Type II, or non-insulin-dependent Diabetes Mellitus Results from an Inability of Insulin Target Tissues to Respond to the Hormone," *Diabetes Mellitus*, 459 (1966).
Foggensteiner et al., "Management of diabetic nephropathy," *Journal of the Royal Society of Medicine*, 94(5):210-217 (2001).
Foo et al., "Mutation of outer-shell residues modulates metal ion co-ordination strength in a metalloenzyme," *Biochemical Journal*, 429:313-321 (2010).
Golay et al., "Link between obesity and type 2 diabetes," *Best Practice & Research Clinical Endocrinology & Metabolism*, 19(4):649-663 (2005).
Hossain et al., "Obesity and Diabetes in the Developing World—A Growing Challenge," *The New England Journal of Medicine*, 356(3):213-215 (2007).
Howard et al., "Obesity and dyslipidemia," *Endocrinology and Metabolism Clinics of North America*, 32:855-867 (2003).
Hsu et al., "Non-homeostatic body weight regulation through a brainstem-restricted receptor for GDF15," *Nature*, 550(7675):255-259 (2017).
Kikkawa, R., "Guidelines for the Treatment of Diabetic Nephropathy," *Asian Medical Journal*, 44(2): 71-75 (2001).
Maric et al., "Obesity, metabolic syndrome and diabetic nephropathy," *Contrib Nephrol.*, 170: 28-35 (2011).
Mooradian, A., "Dyslipidemia in type 2 diabetes mellitus," *Nature Clinical Practice, Endocrinology & Metabolism*, 5(3):150-159 (2009).
Mullican et al., "GFRAL is the receptor for GDF15 and the ligand promotes weight loss in mice and nonhuman primates," *Nature Medicine*, 23(10):1150-1157 (2017).
Sainsbury et al., "Y2 Receptor Deletion Attenuates the Type 2 Diabetic Syndrome of ob/ob Mice," *Diabetes*, 51:3420-3427 (2002).
Styer, "Metabolic Derangements in Diabetes Result from Relative Insulin Insufficiency and Glucagon Excess," *Biochemistry*, 4$^{th}$ Edition, 779-780 (1995).
WHO, "Fight childhood obesity to help prevent diabetes, say WHO & IDF," World Health Organization (2004).
Yang et al., "GFRAL is the receptor for GDF15 and is required for the anti-obesity effects of the ligand," *Nature Medicine*, 23(10):1158-1166 (2017).

\* cited by examiner

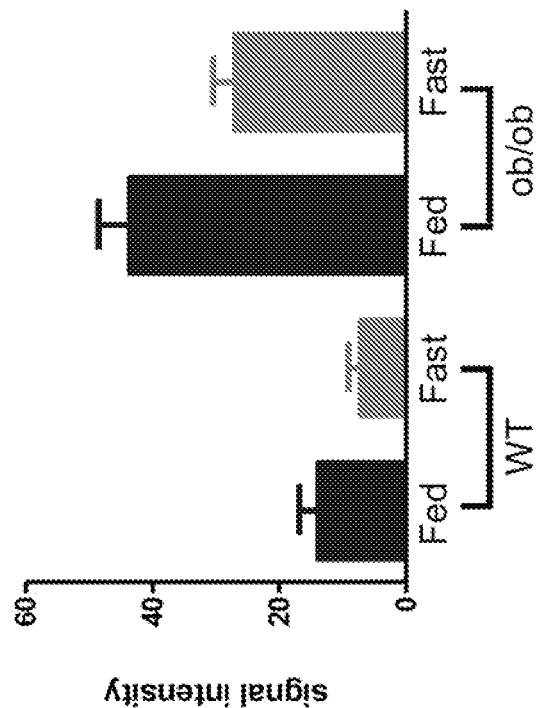
Fig 1B
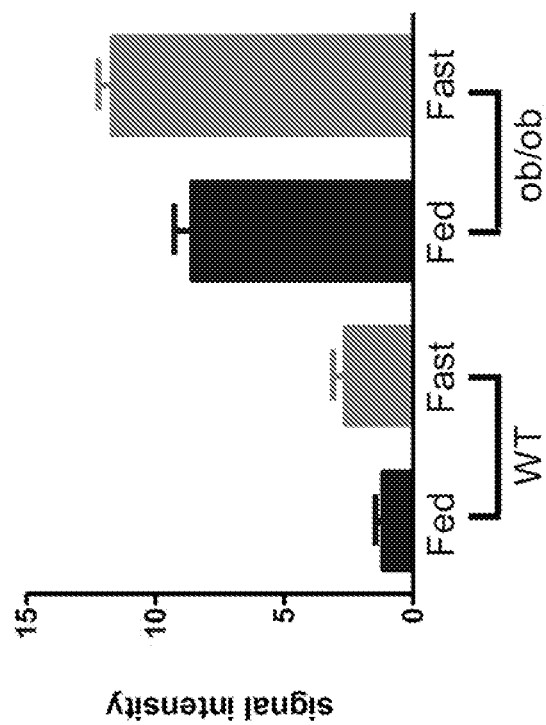
Fig 1A
Figure 1

*** p<0.001

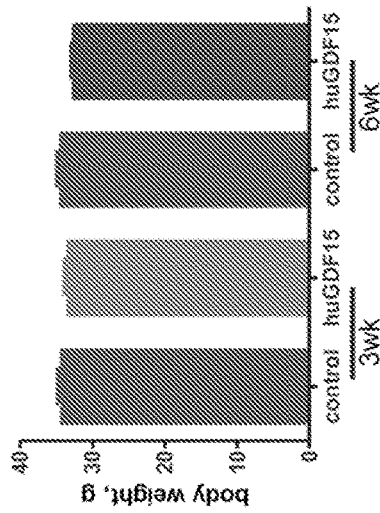
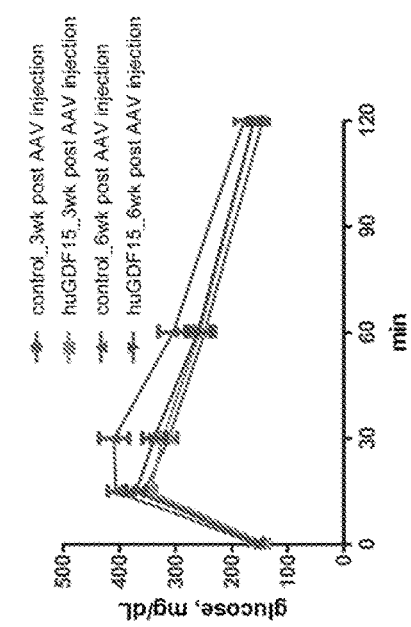
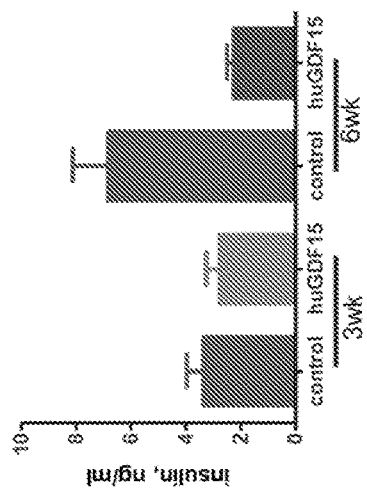
Fig 8A
Fig 8B
Fig 8C
Figure 8

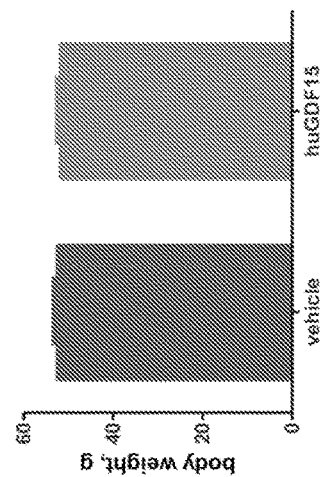
Fig 14A
Fig 14B
Fig 14C
Figure 14

SEQUENCE LISTING

```
<160> NUMBER OF SEQ ID NOS: 14

<210> SEQ ID NO 1
<211> LENGTH: 927
<212> TYPE: DNA
<213> ORGANISM: Homo sapiens
<220> FEATURE:
<221> NAME/KEY: CDS
<222> LOCATION: (1)..(927)

<400> SEQUENCE: 1 atg ccc ggg caa gaa ctc agg acg gtg aat ggc tct cag atg ctc ctg      48
Met Pro Gly Gln Glu Leu Arg Thr Val Asn Gly Ser Gln Met Leu Leu
1               5                  10                  15 gtg ttg ctg gtg ctc tcg tgg ctg ccg cat ggg ggc gcc ctg tct ctg      96
Val Leu Leu Val Leu Ser Trp Leu Pro His Gly Gly Ala Leu Ser Leu
            20                  25                  30 gcc gag gcg agc cgc gca agt ttc ccg gga ccc tca gag ttg cac tcc     144
Ala Glu Ala Ser Arg Ala Ser Phe Pro Gly Pro Ser Glu Leu His Ser
        35                  40                  45
```

```
gaa gac tcc aga ttc cga gag ttg cgg aaa cgc tac gag gac ctg cta      192
Glu Asp Ser Arg Phe Arg Glu Leu Arg Lys Arg Tyr Glu Asp Leu Leu
 50                  55                  60 acc agg ctg cgg gcc aac cag agc tgg gaa gat tcg aac acc gac ctc      240
Thr Arg Leu Arg Ala Asn Gln Ser Trp Glu Asp Ser Asn Thr Asp Leu
 65                  70                  75                  80 gtc ccg gcc cct gca gtc cgg ata ctc acg cca gaa gtg cgg ctg gga      288
Val Pro Ala Pro Ala Val Arg Ile Leu Thr Pro Glu Val Arg Leu Gly
                 85                  90                  95 tcc ggc ggc cac ctg cac ctg cgt atc tct cgg gcc gcc ctt ccc gag      336
Ser Gly Gly His Leu His Leu Arg Ile Ser Arg Ala Ala Leu Pro Glu
            100                 105                 110 ggg ctc ccc gag gcc tcc cgc ctt cac cgg gct ctg ttc cgg ctg tcc      384
Gly Leu Pro Glu Ala Ser Arg Leu His Arg Ala Leu Phe Arg Leu Ser
        115                 120                 125 ccg acg gcg tca agg tcg tgg gac gtg aca cga ccg ctg cgg cgt cag      432
Pro Thr Ala Ser Arg Ser Trp Asp Val Thr Arg Pro Leu Arg Arg Gln
    130                 135                 140 ctc agc ctt gca aga ccc cag gcg ccc gcg ctc cac ctg cga ctg tcg      480
Leu Ser Leu Ala Arg Pro Gln Ala Pro Ala Leu His Leu Arg Leu Ser
145                 150                 155                 160 ccg ccg ccg tcg cag tcg gac caa ctg ctg gca gaa tct tcg tcc gca      528
Pro Pro Pro Ser Gln Ser Asp Gln Leu Leu Ala Glu Ser Ser Ser Ala
                165                 170                 175 cgg ccc cag ctg gag ttg cac ttg cgg ccg caa gcc gcc agg ggg cgc      576
Arg Pro Gln Leu Glu Leu His Leu Arg Pro Gln Ala Ala Arg Gly Arg
            180                 185                 190 cgc aga gcg cgt gcg cgc aac ggg gac cac tgt ccg ctc ggg ccc ggg      624
Arg Arg Ala Arg Ala Arg Asn Gly Asp His Cys Pro Leu Gly Pro Gly
        195                 200                 205 cgt tgc tgc cgt ctg cac acg gtc cgc gcg tcg ctg gaa gac ctg ggc      672
Arg Cys Cys Arg Leu His Thr Val Arg Ala Ser Leu Glu Asp Leu Gly
    210                 215                 220 tgg gcc gat tgg gtg ctg tcg cca cgg gag gtg caa gtg acc atg tgc      720
Trp Ala Asp Trp Val Leu Ser Pro Arg Glu Val Gln Val Thr Met Cys
225                 230                 235                 240 atc ggc gcg tgc ccg agc cag ttc cgg gcg gca aac atg cac gcg cag      768
Ile Gly Ala Cys Pro Ser Gln Phe Arg Ala Ala Asn Met His Ala Gln
                245                 250                 255 atc aag acg agc ctg cac cgc ctg aag ccc gac acg gtg cca gcg ccc      816
Ile Lys Thr Ser Leu His Arg Leu Lys Pro Asp Thr Val Pro Ala Pro
            260                 265                 270 tgc tgc gtg ccc gcc agc tac aat ccc atg gtg ctc att caa aag acc      864
Cys Cys Val Pro Ala Ser Tyr Asn Pro Met Val Leu Ile Gln Lys Thr
        275                 280                 285 gac acc ggg gtg tcg ctc cag acc tat gat gac ttg tta gcc aaa gac      912
Asp Thr Gly Val Ser Leu Gln Thr Tyr Asp Asp Leu Leu Ala Lys Asp
    290                 295                 300 tgc cac tgc ata tga                                                  927
Cys His Cys Ile
305

<210> SEQ ID NO 2
<211> LENGTH: 308
<212> TYPE: PRT
<213> ORGANISM: Homo sapiens

<400> SEQUENCE: 2

Met Pro Gly Gln Glu Leu Arg Thr Val Asn Gly Ser Gln Met Leu Leu
 1               5                  10                  15
```

```
Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
         35                  40                  45

Glu Asp Ser Arg Phe Arg Glu Leu Arg Lys Arg Tyr Glu Asp Leu Leu
     50                  55                  60

Thr Arg Leu Arg Ala Asn Gln Ser Trp Glu Asp Ser Asn Thr Asp Leu
 65                  70                  75                  80

Val Pro Ala Pro Ala Val Arg Ile Leu Thr Pro Glu Val Arg Leu Gly
                 85                  90                  95

Ser Gly Gly His Leu His Leu Arg Ile Ser Arg Ala Ala Leu Pro Glu
                100                 105                 110

Gly Leu Pro Glu Ala Ser Arg Leu His Arg Ala Leu Phe Arg Leu Ser
            115                 120                 125

Pro Thr Ala Ser Arg Ser Trp Asp Val Thr Arg Pro Leu Arg Arg Gln
        130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305

<210> SEQ ID NO 3
<211> LENGTH: 912
<212> TYPE: DNA
<213> ORGANISM: Mus musculus
<220> FEATURE:
<221> NAME/KEY: CDS
<222> LOCATION: (1)..(912)

<400> SEQUENCE: 3 atg gcc ccg ccc gcg ctc cag gcc cag cct cca ggc ggc tct caa ctg    48
Met Ala Pro Pro Ala Leu Gln Ala Gln Pro Pro Gly Gly Ser Gln Leu
 1               5                  10                  15 agg ttc ctg ctg ttc ctg ctg ttg ctg ctg ctg ctg tca tgg cca        96
Arg Phe Leu Leu Phe Leu Leu Leu Leu Leu Leu Leu Ser Trp Pro
            20                  25                  30 tcg cag ggg gac gcc ctg gca atg cct gaa cag cga ccc tcc ggc cct   144
Ser Gln Gly Asp Ala Leu Ala Met Pro Glu Gln Arg Pro Ser Gly Pro
        35                  40                  45
```

```
gag tcc caa ctc aac gcc gac gag cta cgg ggt cgc ttc cag gac ctg     192
Glu Ser Gln Leu Asn Ala Asp Glu Leu Arg Gly Arg Phe Gln Asp Leu
     50                  55                  60 ctg agc cgg ctg cat gcc aac cag agc cga gag gac tcg aac tca gaa     240
Leu Ser Arg Leu His Ala Asn Gln Ser Arg Glu Asp Ser Asn Ser Glu
 65                  70                  75                  80 cca agt cct gac cca gct gtc cgg ata ctc agt cca gag gtg aga ttg     288
Pro Ser Pro Asp Pro Ala Val Arg Ile Leu Ser Pro Glu Val Arg Leu
                 85                  90                  95 ggg tcc cac ggc cag ctg cta ctc cgc gtc aac cgg gcg tcg ctg agt     336
Gly Ser His Gly Gln Leu Leu Leu Arg Val Asn Arg Ala Ser Leu Ser
            100                 105                 110 cag ggt ctc ccc gaa gcc tac cgc gtg cac cga gcg ctg ctc ctg ctg     384
Gln Gly Leu Pro Glu Ala Tyr Arg Val His Arg Ala Leu Leu Leu Leu
        115                 120                 125 acg ccg acg gcc cgc ccc tgg gac atc act agg ccc ctg aag cgt gcg     432
Thr Pro Thr Ala Arg Pro Trp Asp Ile Thr Arg Pro Leu Lys Arg Ala
    130                 135                 140 ctc agc ctc cgg gga ccc cgt gct ccc gca tta cgc ctg cgc ctg acg     480
Leu Ser Leu Arg Gly Pro Arg Ala Pro Ala Leu Arg Leu Arg Leu Thr
145                 150                 155                 160 ccg cct ccg gac ctg gct atg ctg ccc tct ggc ggc acg cag ctg gaa     528
Pro Pro Pro Asp Leu Ala Met Leu Pro Ser Gly Gly Thr Gln Leu Glu
                165                 170                 175 ctg cgc tta cgg gta gcc gcc ggc agg ggg cgc cga agc gcg cat gcg     576
Leu Arg Leu Arg Val Ala Ala Gly Arg Gly Arg Arg Ser Ala His Ala
            180                 185                 190 cac cca aga gac tcg tgc cca ctg ggt ccg ggg cgc tgc tgt cac ttg     624
His Pro Arg Asp Ser Cys Pro Leu Gly Pro Gly Arg Cys Cys His Leu
        195                 200                 205 gag act gtg cag gca act ctt gaa gac ttg ggc tgg agc gac tgg gtg     672
Glu Thr Val Gln Ala Thr Leu Glu Asp Leu Gly Trp Ser Asp Trp Val
    210                 215                 220 ctg tcc ccg cgc cag ctg cag ctg agc atg tgc gtg ggc gag tgt ccc     720
Leu Ser Pro Arg Gln Leu Gln Leu Ser Met Cys Val Gly Glu Cys Pro
225                 230                 235                 240 cac ctg tat cgc tcc gcg aac acg cat gcg cag atc aaa gca cgc ctg     768
His Leu Tyr Arg Ser Ala Asn Thr His Ala Gln Ile Lys Ala Arg Leu
                245                 250                 255 cat ggc ctg cag cct gac aag gtg cct gcc ccg tgc tgt gtc ccc tcc     816
His Gly Leu Gln Pro Asp Lys Val Pro Ala Pro Cys Cys Val Pro Ser
            260                 265                 270 agc tac acc ccg gtg gtt ctt atg cac agg aca gac agt ggt gtg tca     864
Ser Tyr Thr Pro Val Val Leu Met His Arg Thr Asp Ser Gly Val Ser
        275                 280                 285 ctg cag act tat gat gac ctg gtg gcc cgg ggc tgc cac tgc gct tga     912
Leu Gln Thr Tyr Asp Asp Leu Val Ala Arg Gly Cys His Cys Ala
    290                 295                 300

<210> SEQ ID NO 4
<211> LENGTH: 303
<212> TYPE: PRT
<213> ORGANISM: Mus musculus

<400> SEQUENCE: 4

Met Ala Pro Pro Ala Leu Gln Ala Gln Pro Gly Gly Ser Gln Leu
 1               5                  10                  15

Arg Phe Leu Leu Phe Leu Leu Leu Leu Leu Leu Leu Ser Trp Pro
             20                  25                  30
```

```
Ser Gln Gly Asp Ala Leu Ala Met Pro Glu Gln Arg Pro Ser Gly Pro
         35                  40                  45

Glu Ser Gln Leu Asn Ala Asp Glu Leu Arg Gly Arg Phe Gln Asp Leu
 50                  55                  60

Leu Ser Arg Leu His Ala Asn Gln Ser Arg Glu Asp Ser Asn Ser Glu
65                  70                  75                  80

Pro Ser Pro Asp Pro Ala Val Arg Ile Leu Ser Pro Glu Val Arg Leu
                 85                  90                  95

Gly Ser His Gly Gln Leu Leu Leu Arg Val Asn Arg Ala Ser Leu Ser
            100                 105                 110

Gln Gly Leu Pro Glu Ala Tyr Arg Val His Arg Ala Leu Leu Leu Leu
        115                 120                 125

Thr Pro Thr Ala Arg Pro Trp Asp Ile Thr Arg Pro Leu Lys Arg Ala
    130                 135                 140

Leu Ser Leu Arg Gly Pro Arg Ala Pro Ala Leu Arg Leu Arg Leu Thr
145                 150                 155                 160

Pro Pro Pro Asp Leu Ala Met Leu Pro Ser Gly Gly Thr Gln Leu Glu
                165                 170                 175

Leu Arg Leu Arg Val Ala Ala Gly Arg Gly Arg Arg Ser Ala His Ala
            180                 185                 190

His Pro Arg Asp Ser Cys Pro Leu Gly Pro Gly Arg Cys Cys His Leu
        195                 200                 205

Glu Thr Val Gln Ala Thr Leu Glu Asp Leu Gly Trp Ser Asp Trp Val
    210                 215                 220

Leu Ser Pro Arg Gln Leu Gln Leu Ser Met Cys Val Gly Glu Cys Pro
225                 230                 235                 240

His Leu Tyr Arg Ser Ala Asn Thr His Ala Gln Ile Lys Ala Arg Leu
                245                 250                 255

His Gly Leu Gln Pro Asp Lys Val Pro Ala Pro Cys Cys Val Pro Ser
            260                 265                 270

Ser Tyr Thr Pro Val Val Leu Met His Arg Thr Asp Ser Gly Val Ser
        275                 280                 285

Leu Gln Thr Tyr Asp Asp Leu Val Ala Arg Gly Cys His Cys Ala
    290                 295                 300

<210> SEQ ID NO 5
<211> LENGTH: 840
<212> TYPE: DNA
<213> ORGANISM: Homo sapiens
<220> FEATURE:
<221> NAME/KEY: CDS
<222> LOCATION: (1)..(840)

<400> SEQUENCE: 5 ctg tct ctg gcc gag gcg agc cgc gca agt ttc ccg gga ccc tca gag      48
Leu Ser Leu Ala Glu Ala Ser Arg Ala Ser Phe Pro Gly Pro Ser Glu
1               5                  10                  15 ttg cac tcc gaa gac tcc aga ttc cga gag ttg cgg aaa cgc tac gag      96
Leu His Ser Glu Asp Ser Arg Phe Arg Glu Leu Arg Lys Arg Tyr Glu
                 20                  25                  30 gac ctg cta acc agg ctg cgg gcc aac cag agc tgg gaa gat tcg aac     144
Asp Leu Leu Thr Arg Leu Arg Ala Asn Gln Ser Trp Glu Asp Ser Asn
        35                  40                  45 acc gac ctc gtc ccg gcc cct gca gtc cgg ata ctc acg cca gaa gtg     192
Thr Asp Leu Val Pro Ala Pro Ala Val Arg Ile Leu Thr Pro Glu Val
    50                  55                  60 cgg ctg gga tcc ggc ggc cac ctg cac ctg cgt atc tct cgg gcc gcc     240
```

```
                                                              -continued
Arg Leu Gly Ser Gly Gly His Leu His Leu Arg Ile Ser Arg Ala Ala
 65                  70                  75                  80 ctt ccc gag ggg ctc ccc gag gcc tcc cgc ctt cac cgg gct ctg ttc    288
Leu Pro Glu Gly Leu Pro Glu Ala Ser Arg Leu His Arg Ala Leu Phe
                 85                  90                  95 cgg ctg tcc ccg acg gcg tca agg tcg tgg gac gtg aca cga ccg ctg    336
Arg Leu Ser Pro Thr Ala Ser Arg Ser Trp Asp Val Thr Arg Pro Leu
            100                 105                 110 cgg cgt cag ctc agc ctt gca aga ccc cag gcg ccc gcg ctg cac ctg    384
Arg Arg Gln Leu Ser Leu Ala Arg Pro Gln Ala Pro Ala Leu His Leu
        115                 120                 125 cga ctg tcg ccg ccg ccg tcg cag tcg gac caa ctg ctg gca gaa tct    432
Arg Leu Ser Pro Pro Pro Ser Gln Ser Asp Gln Leu Leu Ala Glu Ser
    130                 135                 140 tcg tcc gca cgg ccc cag ctg gag ttg cac ttg cgg ccg caa gcc gcc    480
Ser Ser Ala Arg Pro Gln Leu Glu Leu His Leu Arg Pro Gln Ala Ala
145                 150                 155                 160 agg ggg cgc cgc aga gcg cgt gcg cgc aac ggg gac cac tgt ccg ctc    528
Arg Gly Arg Arg Arg Ala Arg Ala Arg Asn Gly Asp His Cys Pro Leu
                165                 170                 175 ggg ccc ggg cgt tgc tgc cgt ctg cac acg gtc cgc gcg tcg ctg gaa    576
Gly Pro Gly Arg Cys Cys Arg Leu His Thr Val Arg Ala Ser Leu Glu
            180                 185                 190 gac ctg ggc tgg gcc gat tgg gtg ctg tcg cca cgg gag gtg caa gtg    624
Asp Leu Gly Trp Ala Asp Trp Val Leu Ser Pro Arg Glu Val Gln Val
        195                 200                 205 acc atg tgc atc ggc gcg tgc ccg agc cag ttc cgg gcg gca aac atg    672
Thr Met Cys Ile Gly Ala Cys Pro Ser Gln Phe Arg Ala Ala Asn Met
    210                 215                 220 cac gcg cag atc aag acg agc ctg cac cgc ctg aag ccc gac acg gtg    720
His Ala Gln Ile Lys Thr Ser Leu His Arg Leu Lys Pro Asp Thr Val
225                 230                 235                 240 cca gcg ccc tgc tgc gtg ccc gcc agc tac aat ccc atg gtg ctc att    768
Pro Ala Pro Cys Cys Val Pro Ala Ser Tyr Asn Pro Met Val Leu Ile
                245                 250                 255 caa aag acc gac acc ggg gtg tcg ctc cag acc tat gat gac ttg tta    816
Gln Lys Thr Asp Thr Gly Val Ser Leu Gln Thr Tyr Asp Asp Leu Leu
            260                 265                 270 gcc aaa gac tgc cac tgc ata tga                                    840
Ala Lys Asp Cys His Cys Ile
        275

<210> SEQ ID NO 6
<211> LENGTH: 279
<212> TYPE: PRT
<213> ORGANISM: Homo sapiens

<400> SEQUENCE: 6

Leu Ser Leu Ala Glu Ala Ser Arg Ala Ser Phe Pro Gly Pro Ser Glu
 1               5                  10                  15

Leu His Ser Glu Asp Ser Arg Phe Arg Glu Leu Arg Lys Arg Tyr Glu
                20                  25                  30

Asp Leu Leu Thr Arg Leu Arg Ala Asn Gln Ser Trp Glu Asp Ser Asn
            35                  40                  45

Thr Asp Leu Val Pro Ala Pro Ala Val Arg Ile Leu Thr Pro Glu Val
        50                  55                  60

Arg Leu Gly Ser Gly Gly His Leu His Leu Arg Ile Ser Arg Ala Ala
 65                  70                  75                  80

Leu Pro Glu Gly Leu Pro Glu Ala Ser Arg Leu His Arg Ala Leu Phe
```

-continued

```
                85                  90                  95
Arg Leu Ser Pro Thr Ala Ser Arg Ser Trp Asp Val Thr Arg Pro Leu
            100                 105                 110

Arg Arg Gln Leu Ser Leu Ala Arg Pro Gln Ala Pro Ala Leu His Leu
        115                 120                 125

Arg Leu Ser Pro Pro Ser Gln Ser Asp Gln Leu Leu Ala Glu Ser
    130                 135                 140

Ser Ser Ala Arg Pro Gln Leu Glu Leu His Leu Arg Pro Gln Ala Ala
145                 150                 155                 160

Arg Gly Arg Arg Ala Arg Ala Arg Asn Gly Asp His Cys Pro Leu
            165                 170                 175

Gly Pro Gly Arg Cys Cys Arg Leu His Thr Val Arg Ala Ser Leu Glu
        180                 185                 190

Asp Leu Gly Trp Ala Asp Trp Val Leu Ser Pro Arg Glu Val Gln Val
    195                 200                 205

Thr Met Cys Ile Gly Ala Cys Pro Ser Gln Phe Arg Ala Ala Asn Met
    210                 215                 220

His Ala Gln Ile Lys Thr Ser Leu His Arg Leu Lys Pro Asp Thr Val
225                 230                 235                 240

Pro Ala Pro Cys Cys Val Pro Ala Ser Tyr Asn Pro Met Val Leu Ile
            245                 250                 255

Gln Lys Thr Asp Thr Gly Val Ser Leu Gln Thr Tyr Asp Asp Leu Leu
        260                 265                 270

Ala Lys Asp Cys His Cys Ile
        275

<210> SEQ ID NO 7
<211> LENGTH: 816
<212> TYPE: DNA
<213> ORGANISM: Mus musculus
<220> FEATURE:
<221> NAME/KEY: CDS
<222> LOCATION: (1)..(816)

<400> SEQUENCE: 7 tcg cag ggg gac gcc ctg gca atg cct gaa cag cga ccc tcc ggc cct      48
Ser Gln Gly Asp Ala Leu Ala Met Pro Glu Gln Arg Pro Ser Gly Pro
1               5                   10                  15 gag tcc caa ctc aac gcc gac gag cta cgg ggt cgc ttc cag gac ctg      96
Glu Ser Gln Leu Asn Ala Asp Glu Leu Arg Gly Arg Phe Gln Asp Leu
            20                  25                  30 ctg agc cgg ctg cat gcc aac cag agc cga gag gac tcg aac tca gaa     144
Leu Ser Arg Leu His Ala Asn Gln Ser Arg Glu Asp Ser Asn Ser Glu
        35                  40                  45 cca agt cct gac cca gct gtc cgg ata ctc agt cca gag gtg aga ttg     192
Pro Ser Pro Asp Pro Ala Val Arg Ile Leu Ser Pro Glu Val Arg Leu
    50                  55                  60 ggg tcc cac ggc cag ctg cta ctc cgc gtc aac cgg gcg tcg ctg agt     240
Gly Ser His Gly Gln Leu Leu Leu Arg Val Asn Arg Ala Ser Leu Ser
65                  70                  75                  80 cag ggt ctc ccc gaa gcc tac cgc gtg cac cga gcg ctg ctc ctg ctg     288
Gln Gly Leu Pro Glu Ala Tyr Arg Val His Arg Ala Leu Leu Leu Leu
                85                  90                  95 acg ccg acg gcc cgc ccc tgg gac atc act agg ccc ctg aag cgt gcg     336
Thr Pro Thr Ala Arg Pro Trp Asp Ile Thr Arg Pro Leu Lys Arg Ala
            100                 105                 110 ctc agc ctc cgg gga ccc cgt gct ccc gca tta cgc ctg cgc ctg acg     384
Leu Ser Leu Arg Gly Pro Arg Ala Pro Ala Leu Arg Leu Arg Leu Thr
```

```
                115                 120                 125
ccg cct ccg gac ctg gct atg ctg ccc tct ggc ggc acg cag ctg gaa        432
Pro Pro Pro Asp Leu Ala Met Leu Pro Ser Gly Gly Thr Gln Leu Glu
    130                 135                 140 ctg cgc tta cgg gta gcc gcc ggc agg ggg cgc cga agc gcg cat gcg        480
Leu Arg Leu Arg Val Ala Ala Gly Arg Gly Arg Arg Ser Ala His Ala
145                 150                 155                 160 cac cca aga gac tcg tgc cca ctg ggt ccg ggg cgc tgt tgt cac ttg        528
His Pro Arg Asp Ser Cys Pro Leu Gly Pro Gly Arg Cys Cys His Leu
                165                 170                 175 gag act gtg cag gca act ctt gaa gac ttg ggc tgg agc gac tgg gtg        576
Glu Thr Val Gln Ala Thr Leu Glu Asp Leu Gly Trp Ser Asp Trp Val
            180                 185                 190 ctg tcc ccg cgc cag ctg cag ctg agc atg tgc gtg ggc gag tgt ccc        624
Leu Ser Pro Arg Gln Leu Gln Leu Ser Met Cys Val Gly Glu Cys Pro
        195                 200                 205 cac ctg tat cgc tcc gcg aac acg cat gcg cag atc aaa gca cgc ctg        672
His Leu Tyr Arg Ser Ala Asn Thr His Ala Gln Ile Lys Ala Arg Leu
    210                 215                 220 cat ggc ctg cag cct gac aag gtg cct gcc ccg tgc tgt gtc ccc tcc        720
His Gly Leu Gln Pro Asp Lys Val Pro Ala Pro Cys Cys Val Pro Ser
225                 230                 235                 240 agc tac acc ccg gtg gtt ctt atg cac agg aca gac agt ggt gtg tca        768
Ser Tyr Thr Pro Val Val Leu Met His Arg Thr Asp Ser Gly Val Ser
                245                 250                 255 ctg cag act tat gat gac ctg gtg gcc cgg ggc tgc cac tgc gct tga        816
Leu Gln Thr Tyr Asp Asp Leu Val Ala Arg Gly Cys His Cys Ala
            260                 265                 270

<210> SEQ ID NO 8
<211> LENGTH: 271
<212> TYPE: PRT
<213> ORGANISM: Mus musculus

<400> SEQUENCE: 8

Ser Gln Gly Asp Ala Leu Ala Met Pro Glu Gln Arg Pro Ser Gly Pro
1               5                   10                  15

Glu Ser Gln Leu Asn Ala Asp Glu Leu Arg Gly Arg Phe Gln Asp Leu
            20                  25                  30

Leu Ser Arg Leu His Ala Asn Gln Ser Arg Glu Asp Ser Asn Ser Glu
        35                  40                  45

Pro Ser Pro Asp Pro Ala Val Arg Ile Leu Ser Pro Glu Val Arg Leu
    50                  55                  60

Gly Ser His Gly Gln Leu Leu Arg Val Asn Arg Ala Ser Leu Ser
65                  70                  75                  80

Gln Gly Leu Pro Glu Ala Tyr Arg Val His Arg Ala Leu Leu Leu
                85                  90                  95

Thr Pro Thr Ala Arg Pro Trp Asp Ile Thr Arg Pro Leu Lys Arg Ala
            100                 105                 110

Leu Ser Leu Arg Gly Pro Arg Ala Pro Ala Leu Arg Leu Arg Leu Thr
        115                 120                 125

Pro Pro Pro Asp Leu Ala Met Leu Pro Ser Gly Gly Thr Gln Leu Glu
    130                 135                 140

Leu Arg Leu Arg Val Ala Ala Gly Arg Gly Arg Arg Ser Ala His Ala
145                 150                 155                 160

His Pro Arg Asp Ser Cys Pro Leu Gly Pro Gly Arg Cys Cys His Leu
                165                 170                 175
```

```
Glu Thr Val Gln Ala Thr Leu Glu Asp Leu Gly Trp Ser Asp Trp Val
            180                 185                 190
Leu Ser Pro Arg Gln Leu Gln Leu Ser Met Cys Val Gly Glu Cys Pro
        195                 200                 205
His Leu Tyr Arg Ser Ala Asn Thr His Ala Gln Ile Lys Ala Arg Leu
    210                 215                 220
His Gly Leu Gln Pro Asp Lys Val Pro Ala Pro Cys Cys Val Pro Ser
225                 230                 235                 240
Ser Tyr Thr Pro Val Val Leu Met His Arg Thr Asp Ser Gly Val Ser
                245                 250                 255
Leu Gln Thr Tyr Asp Asp Leu Val Ala Arg Gly Cys His Cys Ala
            260                 265                 270

<210> SEQ ID NO 9
<211> LENGTH: 339
<212> TYPE: DNA
<213> ORGANISM: Homo sapiens
<220> FEATURE:
<221> NAME/KEY: CDS
<222> LOCATION: (1)..(339)

<400> SEQUENCE: 9 gcg cgc aac ggg gac cac tgt ccg ctc ggg ccc ggg cgt tgc tgc cgt    48
Ala Arg Asn Gly Asp His Cys Pro Leu Gly Pro Gly Arg Cys Cys Arg
1               5                   10                  15 ctg cac acg gtc cgc gcg tcg ctg gaa gac ctg ggc tgg gcc gat tgg    96
Leu His Thr Val Arg Ala Ser Leu Glu Asp Leu Gly Trp Ala Asp Trp
                20                  25                  30 gtg ctg tcg cca cgg gag gtg caa gtg acc atg tgc atc ggc gcg tgc   144
Val Leu Ser Pro Arg Glu Val Gln Val Thr Met Cys Ile Gly Ala Cys
            35                  40                  45 ccg agc cag ttc cgg gcg gca aac atg cac gcg cag atc aag acg agc   192
Pro Ser Gln Phe Arg Ala Ala Asn Met His Ala Gln Ile Lys Thr Ser
        50                  55                  60 ctg cac cgc ctg aag ccc gac acg gtg cca gcg ccc tgc tgc gtg ccc   240
Leu His Arg Leu Lys Pro Asp Thr Val Pro Ala Pro Cys Cys Val Pro
65                  70                  75                  80 gcc agc tac aat ccc atg gtg ctc att caa aag acc gac acc ggg gtg   288
Ala Ser Tyr Asn Pro Met Val Leu Ile Gln Lys Thr Asp Thr Gly Val
                85                  90                  95 tcg ctc cag acc tat gat gac ttg tta gcc aaa gac tgc cac tgc ata   336
Ser Leu Gln Thr Tyr Asp Asp Leu Leu Ala Lys Asp Cys His Cys Ile
            100                 105                 110 taa                                                               339

<210> SEQ ID NO 10
<211> LENGTH: 112
<212> TYPE: PRT
<213> ORGANISM: Homo sapiens

<400> SEQUENCE: 10

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60
```

```
Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110

<210> SEQ ID NO 11
<211> LENGTH: 351
<212> TYPE: DNA
<213> ORGANISM: Mus musculus
<220> FEATURE:
<221> NAME/KEY: CDS
<222> LOCATION: (1)..(351)

<400> SEQUENCE: 11 atg agc gcg cat gcg cac cca aga gac tcg tgc cca ctg ggt ccg ggg     48
Met Ser Ala His Ala His Pro Arg Asp Ser Cys Pro Leu Gly Pro Gly
 1               5                  10                  15 cgc tgc tgt cac ctg gag act gtg cag gca act ctt gaa gac ttg ggc     96
Arg Cys Cys His Leu Glu Thr Val Gln Ala Thr Leu Glu Asp Leu Gly
            20                  25                  30 tgg agc gac tgg gtg ttg tcc ccg cgc cag ctg cag ctg agc atg tgc    144
Trp Ser Asp Trp Val Leu Ser Pro Arg Gln Leu Gln Leu Ser Met Cys
        35                  40                  45 gtg ggc gag tgt ccc cac ctg tat cgc tcc gcg aac acg cat gcg cag    192
Val Gly Glu Cys Pro His Leu Tyr Arg Ser Ala Asn Thr His Ala Gln
    50                  55                  60 atc aaa gca cgc ctg cat ggc ctg cag cct gac aag gtg cct gcc ccg    240
Ile Lys Ala Arg Leu His Gly Leu Gln Pro Asp Lys Val Pro Ala Pro
 65                 70                  75                  80 tgc tgt gtc ccc tcc agc tac acc ccg gtg gtt ctt atg cac agg aca    288
Cys Cys Val Pro Ser Ser Tyr Thr Pro Val Val Leu Met His Arg Thr
                85                  90                  95 gac agt ggt gtg tca ctg cag act tat gat gac ctg gtg gcc cgg ggc    336
Asp Ser Gly Val Ser Leu Gln Thr Tyr Asp Asp Leu Val Ala Arg Gly
            100                 105                 110 tgc cac tgc gct tga                                                 351
Cys His Cys Ala
        115

<210> SEQ ID NO 12
<211> LENGTH: 116
<212> TYPE: PRT
<213> ORGANISM: Mus musculus

<400> SEQUENCE: 12

Met Ser Ala His Ala His Pro Arg Asp Ser Cys Pro Leu Gly Pro Gly
 1               5                  10                  15

Arg Cys Cys His Leu Glu Thr Val Gln Ala Thr Leu Glu Asp Leu Gly
            20                  25                  30

Trp Ser Asp Trp Val Leu Ser Pro Arg Gln Leu Gln Leu Ser Met Cys
        35                  40                  45

Val Gly Glu Cys Pro His Leu Tyr Arg Ser Ala Asn Thr His Ala Gln
    50                  55                  60

Ile Lys Ala Arg Leu His Gly Leu Gln Pro Asp Lys Val Pro Ala Pro
 65                 70                  75                  80

Cys Cys Val Pro Ser Ser Tyr Thr Pro Val Val Leu Met His Arg Thr
                85                  90                  95

Asp Ser Gly Val Ser Leu Gln Thr Tyr Asp Asp Leu Val Ala Arg Gly
```

```
                100             105             110
Cys His Cys Ala
        115

<210> SEQ ID NO 13
<211> LENGTH: 4
<212> TYPE: PRT
<213> ORGANISM: Mus musculus

<400> SEQUENCE: 13

Arg Gly Arg Arg
1

<210> SEQ ID NO 14
<211> LENGTH: 7
<212> TYPE: PRT
<213> ORGANISM: Homo sapiens

<400> SEQUENCE: 14

Arg Gly Arg Arg Arg Ala Arg
1               5
```

METHOD OF TREATING OR AMELIORATING METABOLIC DISORDERS USING GROWTH DIFFERENTIATION FACTOR 15 (GDF-15)

This application claims the benefit of U.S. Provisional Application No. 61/473,583 filed Apr. 8, 2011, which is incorporated in its entirety by reference herein.

FIELD OF THE INVENTION

The disclosed invention relates to the treatment or amelioration of a metabolic disorder, such as Type 2 diabetes, elevated glucose levels, elevated insulin levels, dyslipidemia, obesity or diabetic nephropathy, by administering a therapeutically effective amount of GDF15 to a subject in need thereof.

BACKGROUND OF THE INVENTION

Growth differentiation factor 15 (GDF15) is a divergent member of the TGFβ superfamily. It is also called macrophage inhibitory cytokine 1 (MIC1) (Bootcov M R, 1997, *Proc Natl Acad Sci* 94:11514-9.), placental bone morphogenetic factor (PLAB) (Hromas R 1997, *Biochim Biophys Acta.* 1354:40-4.), placental transforming growth factor beta (PTGFB) (Lawton L N 1997, *Gene.* 203:17-26), prostate derived factor (PDF) (Paralkar V M 1998, *J Biol Chem.* 273:13760-7), and nonsteroidal anti-inflammatory drug-activated gene (NAG-1) (Baek S J 2001, *J Biol Chem.* 276: 33384-92).

Human GDF15 gene is located on chromosome 19p13.2-13.1; rat GDF15 gene is located on chromosome 16; and mouse GDF15 gene is located on chromosome 8. The GDF15 open reading frames span two exons (Bottner M 1999, *Gene.* 237:105-11 and NCBI). The mature GDF15 peptide shares low homology with other family members (Katoh M 2006, *Int J Mol Med.* 17:951-5.).

GDF15 is synthesized as a large precursor protein that is cleaved at the dibasic cleavage site to release the carboxy-terminal mature peptide. The mouse and rat GDF15 prepropeptides both contain 303 amino acids. Human full-length precursor contains 308 amino acids. The rodent mature peptides contain 115 amino acids after processing at the RGRR (SEQ ID NO:13) cleavage site. The human mature peptide contains 112 amino acids after processing at the RGRRRAR (SEQ ID NO:14) cleavage site. Human mature GDF15 peptide shared 66.1% and 68.1% sequence similarity with rat and mouse mature GDF15 peptides (Bottner M 1999, *Gene.* 237:105-11; Bauskin A R 2000, *EMBO J.* 19:2212-20; NCBI). There is no glycosylation site in the mature GDF15 peptide.

The mature GDF15 peptide contains the seven conserved cysteine residues required for the formation of the cysteine knot motif and the single interchain disulfide bond that are typical for TGFβ superfamily members. The mature peptide further contains two additional cysteine residues that form a fourth intrachain disulfide bond. Biologically active GDF15 is a 25 kD homodimer of the mature peptide covalently linked by one interchain disulfide bond.

GDF15 circulating levels have been reported to be elevated in multiple pathological and physiological conditions, most notably pregnancy (Moore A G 2000. *J Clin Endocrinol Metab* 85: 4781-4788), β-thalassemia (Tanno T 2007, Nat Med 13:1096-101) (Zimmermann M B, 2008 *Am J Clin Nutr* 88:1026-31), congenital dyserythropoietic anemia (Tamary H 2008, *Blood.* 112:5241-4). GDF15 has also been linked to multiple biological activities in literature reports. Studies of GDF15 knockout and transgenic mice suggested that GDF15 may be protective against ischemic/reperfusion- or overload-induced heart injury (Kempf T, 2006, *Circ Res.*98:351-60) (Xu J, 2006, *Circ Res.* 98:342-50), protective against aging-associated motor neuron and sensory neuron loss (Strelau J, 2009, *J Neurosci.* 29:13640-8.), mildly protective against metabolic acidosis in kidney, and may cause cachexia in cancer patients (Johnen H 2007 *Nat Med.* 11:1333-40). Many groups also studied the role of GDF15 in cell apoptosis and proliferation and reported controversial results using different cell culture and xenograft models. Studies on transgenic mice showed that GDF15 is protective against carcinogen or Apc mutation induced neoplasia in intestine and lung (Baek S J 2006, *Gastroenterology.* 131:1553-60) (Cekanova M 2009, *Cancer Prev Res* 2:450-8.).

SUMMARY OF THE INVENTION

A method of treating a metabolic disorder is provided. In one embodiment the method comprises administering to a subject in need thereof a therapeutically effective amount of an isolated human GDF15 polypeptide. In various embodiments, the metabolic disorder is type 2 diabetes, dyslipidemia, obesity, or diabetic nephropathy. In other embodiments, the metabolic disorder comprises a condition in which the subject has a fasting blood glucose level of greater than or equal to 100 mg/dL. The subject on which the method is performed can be a mammal, for example a human. In specific embodiments the GDF15 protein comprises one of SEQ ID NOS:2, 6 and 10 and/or is encoded by the nucleic acid sequence of SEQ ID NO:9. In some embodiments the GDF15 polypeptide is administered in the form of a pharmaceutical composition comprising the GDF15 polypeptide in admixture with a pharmaceutically-acceptable carrier. In yet other embodiments the provided method further comprises the step of determining the subject's blood glucose level at a timepoint subsequent to the administration. In still other embodiments the method further comprises the step of determining the subject's serum insulin level at a timepoint subsequent to the administration.

Also provided is another method of treating a metabolic disorder. In one embodiment the method comprises administering to a subject in need thereof a therapeutically effective amount of an isolated human GDF15 polypeptide comprising an amino acid sequence that has at least 90% sequence identity with one of SEQ ID NOS:2, 6 and 10. In various embodiments, the metabolic disorder is type 2 diabetes, dyslipidemia, obesity, or diabetic nephropathy. In other embodiments, the metabolic disorder comprises a condition in which the subject has a fasting blood glucose level of greater than or equal to 100 mg/dL. The subject on which the method is performed can be a mammal, for example a human. In specific embodiments the GDF15 protein comprises one of SEQ ID NOS:2, 6 and 10 and/or is encoded by one SEQ ID NOS:1, 5 and 9. In some embodiments the GDF15 polypeptide is administered in the form of a pharmaceutical composition comprising the GDF15 polypeptide in admixture with a pharmaceutically-acceptable carrier. In yet other embodiments the provided method further comprises the step of determining the subject's blood glucose level at a timepoint subsequent to the administration. In still other embodiments the method further comprises the step of determining the subject's serum insulin level at a timepoint subsequent to the administration.

BRIEF DESCRIPTION OF THE DRAWINGS

FIG. 1 is a series of two bar graphs showing the regulation of GDF15 expression in murine liver (FIG. 1A) and murine fat (FIG. 1B) by nutritional states.

FIG. 4B shows body weight over time in mice fed ad libitum treated with control or GDF15 AAV and in mice pair fed injected with control AAV; FIG. 4C shows plasma glucose levels at the end of the pair-feeding study; and FIG. 4D shows body weight at the end of the pair-feeding study.

FIGS. 6A and 6B show the plasma glucose and plasma insulin levels, respectively, measured during OGTT three weeks post AAV injection, and FIGS. 6C and 6D show plasma glucose and plasma glucose/basal glucose levels measured during ITT two weeks post AAV injection.

FIG. 8 is a plot and two bar graphs showing the effect of AAV-mediated human GDF15 on the progression of glucose intolerance in KKAy mice; FIG. 8A shows plasma glucose levels during an OGTT; FIG. 8B body weight 3 weeks and 6 weeks after AAV injection; and FIG. 8C insulin levels 3 weeks and 6 weeks after AAV injection.

FIG. 9A shows urine glucose levels; FIG. 9B urine volume; FIG. 9C glucose excretion; FIG. 9D urine albumin; FIG. 9E albumin excretion; FIG. 9F water intake; FIG. 9G insulin levels; FIG. 9H plasma glucose levels; FIG. 9I human GDF15 levels; FIG. 9J shows body weight and FIG. 9K food intake.

FIG. 11A shows body weight; FIG. 11B the amount of human GDF15 expressed; FIG. 11C total body mass; FIG. 11D fat mass; FIG. 11E non-fat mass; FIG. 11F bone mineral density; FIG. 11G percent of fat mass/body mass; and FIG. 11H percent of non-fat mass/total body mass.

FIG. 12A shows plasma glucose levels; FIG. 12B body weight; and FIG. 12C food intake at day 1 and 2 after the injection of vehicle or murine GDF15.

FIG. 13A shows plasma glucose levels; FIG. 13B food intake; and FIG. 13C body weight.

FIG. 14 is a series of a plot and two bar graphs showing the effect of recombinant human GDF15 in DIO mice; FIG. 14A shows plasma glucose levels measured during OGTT 3 days after protein injection; FIG. 14B food intake; and FIG. 14C body weight.

FIG. 15A shows plasma triglyceride levels during the lipid tolerance test; and FIG. 15B shows plasma exposure of recombinant human GDF15.

FIG. 16A shows plasma insulin levels; FIG. 16B non-esterified fatty acid (NEFA) levels; FIG. 16C total cholesterol levels; and FIG. 16D triglyceride levels.

DETAILED DESCRIPTION OF THE INVENTION

Figure 2:
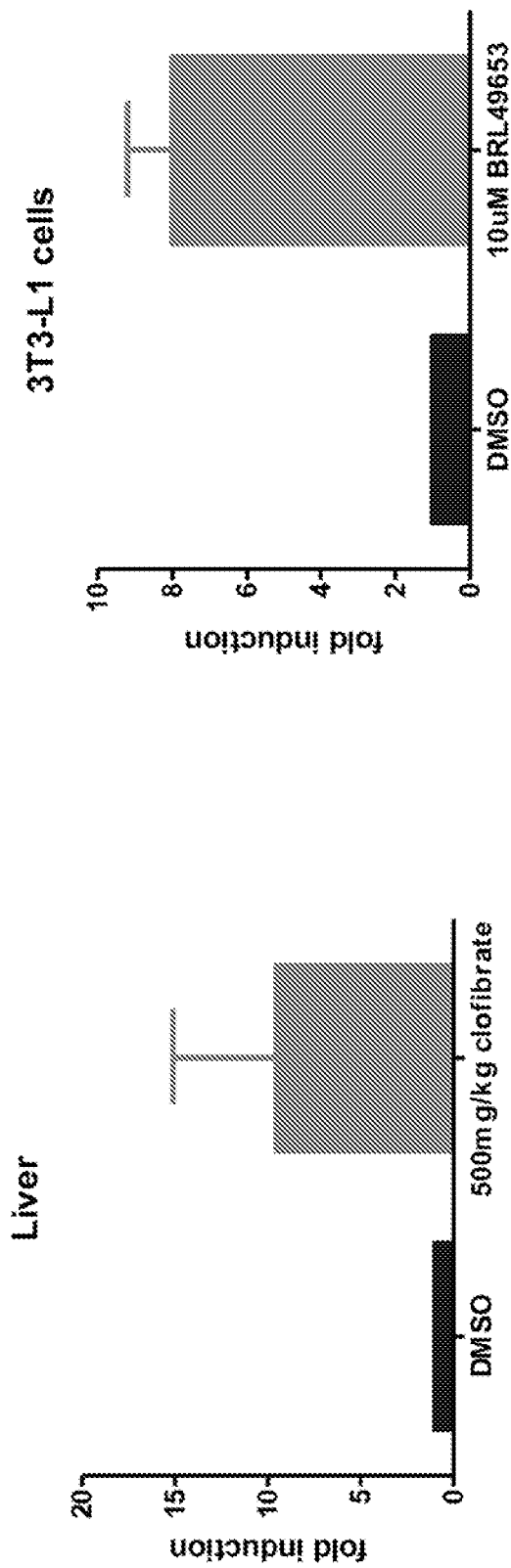
FIG. 2 is a series of two bar graphs showing the upregulation of GDF15 expression in murine liver (FIG. 2A) and murine 3T3-L1 adipocytes (FIG. 2B) by PPAR agonists.

The instant disclosure provides a method of treating a metabolic disorder, such as Type 2 diabetes mellitus (referred to interchangeably herein as "type 2 diabetes"), elevated glucose levels, elevated insulin levels, dyslipidemia or obesity, by administering to a subject in need thereof a therapeutically effective amount of an isolated human GDF15 polypeptide. Methods of administration and delivery are also provided.

Recombinant polypeptide and nucleic acid methods used herein, included in the Examples, are generally those set forth in Sambrook et al., *Molecular Cloning: A Laboratory Manual* (Cold Spring Harbor Laboratory Press, 1989) and subsequent editions or *Current Protocols in Molecular Biology* (Ausubel et al., eds., Green Publishers Inc. and Wiley and Sons 1994) and subsequent editions, both of which are incorporated herein by reference for any purpose.

I. General Definitions

Following convention, as used herein "a" and "an" mean "one or more" unless specifically indicated otherwise.

As used herein, the terms "amino acid" and "residue" are interchangeable and, when used in the context of a peptide or polypeptide, refer to both naturally occurring and synthetic amino acids, as well as amino acid analogs, amino acid mimetics and non-naturally occurring amino acids that are chemically similar to the naturally occurring amino acids.

A "naturally occurring amino acid" is an amino acid that is encoded by the genetic code, as well as those amino acids that are encoded by the genetic code that are modified after synthesis, e.g., hydroxyproline, γ-carboxyglutamate, and O-phosphoserine. An amino acid analog is a compound that has the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but will retain the same basic chemical structure as a naturally occurring amino acid.

An "amino acid mimetic" is a chemical compound that has a structure that is different from the general chemical structure of an amino acid, but that functions in a manner similar to a naturally occurring amino acid. Examples include a methacryloyl or acryloyl derivative of an amide, β-, γ-, δ-imino acids (such as piperidine-4-carboxylic acid) and the like.

A "non-naturally occurring amino acid" is a compound that has the same basic chemical structure as a naturally occurring amino acid, but is not incorporated into a growing polypeptide chain by the translation complex. "Non-naturally occurring amino acid" also includes, but is not limited to, amino acids that occur by modification (e.g., posttranslational modifications) of a naturally encoded amino acid (including but not limited to, the 20 common amino acids) but are not themselves naturally incorporated into a growing polypeptide chain by the translation complex. A non-limiting lists of examples of non-naturally occurring amino acids that can be inserted into a polypeptide sequence or substituted for a wild-type residue in polypeptide sequence include β-amino acids, homoamino acids, cyclic amino acids and amino acids with derivatized side chains. Examples include (in the L-form or D-form; abbreviated as in parentheses): citrulline (Cit), homocitrulline (hCit), Nα-methylcitrulline (NMeCit), Nα-methylhomocitrulline (Naα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMcR), Nα-methylleucine (Nα-McL or NMcL), N-methylhomolysine (NMeHoK), Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl)alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α, β-diaminopropionoic acid (Dpr), α, γ-diaminobutyric acid (Dab), diaminopropionic acid (Dap), cyclohexylalanine (Cha), 4-methyl-phenylalanine (MePhe), β, β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allohydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), and other similar amino acids, and derivatized forms of any of those specifically listed.

The term "isolated nucleic acid molecule" refers to a single or double-stranded polymer of deoxyribonucleotide or ribonucleotide bases read from the 5' to the 3' end (e.g., a GDF15 nucleic acid sequence provided herein), or an analog thereof, that has been separated from at least about 50 percent of polypeptides, peptides, lipids, carbohydrates, polynucleotides or other materials with which the nucleic acid is naturally found when total nucleic acid is isolated from the source cells. Preferably, an isolated nucleic acid molecule is substantially free from any other contaminating nucleic acid molecules or other molecules that are found in the natural environment of the nucleic acid that would interfere with its use in polypeptide production or its therapeutic, diagnostic, prophylactic or research use.

The terms "isolated polypeptide" and "isolated protein" are used interchangeably and refer to a polypeptide (e.g., a GDF15 polypeptide provided herein) that has been separated from at least about 50, 60, 70, 80, 85, 90, 95, 96, 97, 98, or 99 percent of the polypeptides, peptides, lipids, carbohydrates, polynucleotides, or other materials with which the polypeptide is naturally found when isolated from a source cell. Preferably, the isolated polypeptide is substantially free from any other contaminating polypeptides or other contaminants that are found in its natural environment that would interfere with its therapeutic, diagnostic, prophylactic or research use.

The term "encoding" refers to a polynucleotide sequence encoding one or more amino acids. The term does not require a start or stop codon. An amino acid sequence can be encoded in any one of six different reading frames provided by a polynucleotide sequence.

The terms "identical" and percent "identity," in the context of two or more nucleic acids or polypeptide sequences, refer to two or more sequences or subsequences that are the same. "Percent identity" means the percent of identical residues between the amino acids or nucleotides in the compared molecules and is calculated based on the size of the smallest of the molecules being compared. For these calculations, gaps in alignments (if any) can be addressed by a particular mathematical model or computer program (i.e., an "algorithm") Methods that can be used to calculate the identity of the aligned nucleic acids or polypeptides include those described in, e.g., *Computational Molecular Biology*, (Lesk, A. M., ed.), (1988) New York: Oxford University Press; *Biocomputing Informatics and Genome Projects*, (Smith, D. W., ed.), 1993, New York: Academic Press; *Computer Analysis of Sequence Data, Part I*, (Griffin, A. M., and Griffin, H. G., eds.), 1994, New Jersey: Humana Press; von Heinje, G., (1987) *Sequence Analysis in Molecular Biology*, New York: Academic Press; Sequence Analysis Primer, (Gribskov, M. and Devereux, J., eds.), 1991, New York: M. Stockton Press; and Carillo et al., (1988) *SIAM J. Applied Math.* 48:1073.

In calculating percent identity, the sequences being compared are aligned in a way that gives the largest match between the sequences. The computer program used to determine percent identity is the GCG program package, which includes GAP (Devereux et al., (1984) *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually ¹⁄₁₀ times the gap opening penalty), as well as a comparison matrix such as PAM 250 or BLOSUM 62 are used in conjunction with the algorithm. In certain embodiments, a standard comparison matrix (see, Dayhoff et al., (1978) *Atlas of Protein Sequence and Structure* 5:345-352 for the PAM 250 comparison matrix; Henikoff et al., (1992) *Proc. Natl. Acad. Sci. U.S.A.* 89:10915-10919 for the BLOSUM 62 comparison matrix) is also used by the algorithm.

Recommended parameters for determining percent identity for polypeptides or nucleotide sequences using the GAP program are the following:

Algorithm: Needleman et al., 1970, *J. Mol. Biol.* 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

The terms "GDF15 polypeptide" and "GDF15 protein" are used interchangeably and mean a naturally-occurring wild-type polypeptide expressed in a mammal, such as a human or a mouse. For purposes of this disclosure, the term "GDF15 polypeptide" can be used interchangeably to refer to any full-length GDF15 polypeptide, e.g., SEQ ID NO:2, which consist of 308 amino acid residues and which is encoded by the nucleotide sequence SEQ ID NOs:1 (which, when expressed recombinantly, may but need not comprise a stop codon); any form comprising the active and prodomains of the polypeptide, e.g., SEQ ID NO:6, which consist of 279 amino acid residues and which is encoded by the nucleotide sequence SEQ ID NO:5 (which, when expressed recombinantly, may but need not comprise a stop codon), and in which the 29 amino acid residues at the amino-terminal end of the full-length GDF15 polypeptide (i.e., which constitute the signal peptide) have been removed; and any form of the polypeptide comprising the active domain from which the prodomain and signal sequence have been removed, e.g., SEQ ID NO:10, which consists of 112 amino acid residues and which is encoded by the nucleotide sequence SEQ ID NO:9 (which, when expressed recombinantly, may but need not comprise a stop codon), in which the signal sequence and the pro domain have been removed. GDF15 polypeptides can but need not comprise an amino-terminal methionine, which may be introduced by engineering or as a result of a bacterial expression process.

The term "GDF15 polypeptide" also encompasses a GDF15 polypeptide in which a naturally occurring GDF15 polypeptide sequence (e.g., SEQ ID NOs:2, 6 or 10) has been modified. Such modifications include, but are not limited to, one or more amino acid substitutions, including substitutions with non-naturally occurring amino acids non-naturally-occurring amino acid analogs and amino acid mimetics.

In various embodiments, a GDF15 polypeptide comprises an amino acid sequence that is at least about 85 percent identical to a naturally-occurring GDF15 polypeptide (e.g., SEQ ID NOs:2, 6 or 10). In other embodiments, a GDF15 polypeptide comprises an amino acid sequence that is at least about 90 percent, or about 95, 96, 97, 98, or 99 percent identical to a naturally-occurring GDF15 polypeptide amino acid sequence (e.g., SEQ ID NOs:2, 6 or 10). Such GDF15 polypeptides preferably, but need not, possess at least one activity of a wild-type GDF15 polypeptide, such as the ability to lower blood glucose, insulin, triglyceride, or cholesterol levels; the ability to reduce body weight; or the ability to improve glucose tolerance, energy expenditure, or insulin sensitivity. The present invention also encompasses nucleic acid molecules encoding such GDF15 polypeptide sequences. As stated herein, a GDF15 polypeptide can comprise a signal sequence (residues 1-29 of SEQ ID NO:2) or it can have the signal sequence removed (providing SEQ ID NO:6). In other embodiments, a human GDF15 polypeptide can have the signal sequence removed and can also be cleaved at residue 198, separating the primary sequence of the prodomain (residues 30-198 of SEQ ID NO:2) from the primary sequence of the active domain. The naturally-occurring biologically active form of the GDF15 polypeptide is a homodimer of the processed mature peptide (residues 199-308 of SEQ ID NO:2). In some instances, a GDF15 polypeptide can be used to treat or ameliorate a metabolic disorder in a subject is a mature form of GDF15 polypeptide that is derived from the same species as the subject.

A GDF15 polypeptide is preferably biologically active. In various respective embodiments, a GDF15 polypeptide has a biological activity that is equivalent to, greater to or less than that of the naturally occurring form of the mature GDF15 protein from which the signal peptide has been removed from the N-terminus of the full length GDF15 sequence and in which the prodomain has been cleaved (but not necessarily removed from) the active domain. Examples of biological activities include the ability to lower blood glucose, insulin, triglyceride, or cholesterol levels; the ability to reduce body weight; or the ability to improve glucose tolerance, lipid tolerance, or insulin sensitivity; the ability to lower urine glucose and protein excretion.

The terms "therapeutically effective dose" and "therapeutically effective amount," as used herein, means an amount of GDF15 polypeptide that elicits a biological or medicinal response in a tissue system, animal, or human being sought by a researcher, physician, or other clinician, which includes alleviation or amelioration of the symptoms of the disease or disorder being treated, i.e., an amount of a GDF15 polypeptide that supports an observable level of one or more desired biological or medicinal response, for example lowering blood glucose, insulin, triglyceride, or cholesterol levels; reducing body weight; or improving glucose tolerance, energy expenditure, or insulin sensitivity.

II. GDF15 Polypeptides and Nucleic Acids

As disclosed herein, a GDF15 polypeptide described by the instant disclosure can be engineered and/or produced using standard molecular biology methodology. In various examples, a nucleic acid sequence encoding a GDF15, which can comprise all or a portion of SEQ ID NOs:2, 6 or 10 can be isolated and/or amplified from genomic DNA, or cDNA using appropriate oligonucleotide primers. Primers can be designed based on the nucleic and amino acid sequences provided herein according to standard (RT)-PCR amplification techniques. The amplified GDF15 nucleic acid can then be cloned into a suitable vector and characterized by DNA sequence analysis.

Oligonucleotides for use as probes in isolating or amplifying all or a portion of the GDF15 sequences provided herein can be designed and generated using standard synthetic techniques, e.g., automated DNA synthesis apparatus, or can be isolated from a longer sequence of DNA.

II.A. Naturally-Occurring and Variant GDF15 Polypeptide and Polynucleotide Sequences In vivo, GDF15 is expressed as a contiguous amino acid sequence comprising a signal sequence, a pro domain and an active domain.

The 308 amino acid sequence of full length human GDF15 is (shown with an optional N-terminal methionine codon in parentheses):

(SEQ ID NO: 2)
(M)PGQELRTVNGSQMLLVLLVLSWLPHGGALSLAEASRASFPGPSELHS

EDSRFRELRKRYEDLLTRLRANQSWEDSNTDLVPAPAVRILTPEVRLGSG

GHLHLRISRAALPEGLPEASRLHRALFRLSPTASRSWDVTRPLRRQLSLA

RPQAPALHLRLSPPPSQSDQLLAESSSARPQLELHLRPQAARGRRRARAR

NGDHCPLGPGRCCRLHTVRASLEDLGWADWVLSPREVQVTMCIGACPSQF

RAANMHAQIKTSLHRLKPDTVPAPCCVPASYNPMVLIQKTDTGVSLQTYD

DLLAKDCHCI and is encoded by the DNA sequence (shown with an optional N-terminal methionine codon in parentheses, and optional stop codon):

(SEQ ID NO: 1)
(ATG)CCCGGGCAAGAACTCAGGACGGTGAATGGCTCTCAGATGCTCCTG

GTGTTGCTGGTGCTCTCGTGGCTGCCGCATGGGGGCGCCCTGTCTCTGGC

CGAGGCGAGCCGCGCAAGTTTCCCGGGACCCTCAGAGTTGCACTCCGAAG

ACTCCAGATTCCGAGAGTTGCGGAAACGCTACGAGGACCTGCTAACCAGG

CTGCGGGCCAACCAGAGCTGGGAAGATTCGAACACCGACCTCGTCCCGGC

CCCTGCAGTCCGGATACTCACGCCAGAAGTGCGGCTGGGATCCGGCGGCC

ACCTGCACCTGCGTATCTCTCGGGCCGCCCTTCCCGAGGGGCTCCCCGAG

GCCTCCCGCCTTCACCGGGCTCTGTTCCGGCTGTCCCCGACGGCGTCAAG

GTCGTGGGACGTGACACGACCGCTGCGGCGTCAGCTCAGCCTTGCAAGAC

CCCAGGCGCCCGCGCTGCACCTGCGACTGTCGCCGCCGCCGTCGCAGTCG

GACCAACTGCTGGCAGAATCTTCGTCCGCACGGCCCCAGCTGGAGTTGCA

CTTGCGGCCGCAAGCCGCCAGGGGGCGCCGCAGAGCGCGTGCGCGCAACG

GGGACCACTGTCCGCTCGGGCCCGGGCGTTGCTGCCGTCTGCACACGGTC

CGCGCGTCGCTGGAAGACCTGGGCTGGGCCGATTGGGTGCTGTCGCCACG

GGAGGTGCAAGTGACCATGTGCATCGGCGCGTGCCCGAGCCAGTTCCGGG

CGGCAAACATGCACGCGCAGATCAAGACGAGCCTGCACCGCCTGAAGCCC

GACACGGTGCCAGCGCCCTGCTGCGTGCCCGCCAGCTACAATCCCATGGT

GCTCATTCAAAAGACCGACACCGGGGTGTCGCTCCAGACCTATGATGACT

TGTTAGCCAAAGACTGCCACTGCATATGA.

The 303 amino acid sequence of full length murine GDF15 is (shown with an optional N-terminal methionine codon in parentheses):

(SEQ ID NO: 4)
(M)APPALQAQPPGGSQLRFLLFLLLLLLLLSWPSQGDALAMPEQRPSGP

ESQLNADELRGRFQDLLSRLHANQSREDSNSEPSPDPAVRILSPEVRLGS

HGQLLLRVNRASLSQGLPEAYRVHRALLLLTPTARPWDITRPLKRALSLR

GPRAPALRLRLTPPPDLAMLPSGGTQLELRLRVAAGRGRRSAHAHPRDSC

PLGPGRCCHLETVQATLEDLGWSDWVLSPRQLQLSMCVGECPHLYRSANT

HAQIKARLHGLQPDKVPAPCCVPSSYTPVVLMHRTDSGVSLQTYDDLVAR

GCHCA and is encoded by the DNA sequence (shown with an optional N-terminal methionine codon in parentheses, and optional stop codon):

(SEQ ID NO: 3)
(ATG)GCCCCGCCCGCGCTCCAGGCCCAGCCTCCAGGCGGCTCTCAACTG

AGGTTCCTGCTGTTCCTGCTGCTGTTGCTGCTGCTGCTGTCATGGCCATC

GCAGGGGACGCCCTGGCAATGCCTGAACAGCGACCCTCCGGCCCTGAGT

CCCAACTCAACGCCGACGAGCTACGGGGTCGCTTCCAGGACCTGCTGAGC

CGGCTGCATGCCAACCAGAGCCGAGAGGACTCGAACTCAGAACCAAGTCC

TGACCCAGCTGTCCGGATACTCAGTCCAGAGGTGAGATTGGGGTCCCACG

GCCAGCTGCTACTCCGCGTCAACCGGGCGTCGCTGAGTCAGGGTCTCCCC

GAAGCCTACCGCGTGCACCGAGCGCTGCTCCTGCTGACGCCGACGGCCCG

CCCCTGGGACATCACTAGGCCCCTGAAGCGTGCGCTCAGCCTCCGGGGAC

CCCGTGCTCCCGCATTACGCCTGCGCCTGACGCCGCCTCCGGACCTGGCT

ATGCTGCCCTCTGGCGGCACGCAGCTGGAACTGCGCTTACGGGTAGCCGC

CGGCAGGGGCGCCGAAGCGCGCATGCGCACCCAAGAGACTCGTGCCCAC

TGGGTCCGGGCGCTGCTGTCACTTGGAGACTGTGCAGGCAACTCTTGAA

GACTTGGGCTGGAGCGACTGGGTGCTGTCCCCGCGCCAGCTGCAGCTGAG

CATGTGCGTGGGCGAGTGTCCCCACCTGTATCGCTCCGCGAACACGCATG

CGCAGATCAAAGCACGCCTGCATGGCCTGCAGCCTGACAAGGTGCCTGCC

-continued
```
CCGTGCTGTGTCCCCTCCAGCTACACCCCGGTGGTTCTTATGCACAGGAC

AGACAGTGGTGTGTCACTGCAGACTTATGATGACCTGGTGGCCCGGGGCT

GCCACTGCGCTTGA.
```

The amino acid sequence of human GDF15 following cleavage of the 29 residue signal sequence is (shown with an optional N-terminal methionine codon in parentheses):

```
                                     (SEQ ID NO: 6)
(M)LSLAEASRASFPGPSELHSEDSRFRELRKRYEDLLTRLRANQSWEDS

NTDLVPAPAVRILTPEVRLGSGGHLHLRISRAALPEGLPEASRLHRALFR

LSPTASRSWDVTRPLRRQLSLARPQAPALHLRLSPPPSQSDQLLAESSSA

RPQLELHLRPQAARGRRRARARNGDHCPLGPGRCCRLHTVRASLEDLGWA

DWVLSPREVQVTMCIGACPSQFRAANMHAQIKTSLHRLKPDTVPAPCCVP

ASYNPMVLIQKTDTGVSLQTYDDLLAKDCHCI
``` and is encoded by the DNA sequence (shown with an optional N-terminal methionine codon in parentheses, and optional stop codon):

```
                                     (SEQ ID NO: 5)
(ATG)CTGTCTCTGGCCGAGGCGAGCCGCGCAAGTTTCCCGGGACCCTCA

GAGTTGCACTCCGAAGACTCCAGATTCCGAGAGTTGCGGAAACGCTACGA

GGACCTGCTAACCAGGCTGCGGGCCAACCAGAGCTGGGAAGATTCGAACA

CCGACCTCGTCCCGGCCCCTGCAGTCCGGATACTCACGCCAGAAGTGCGG

CTGGGATCCGGCGGCCACCTGCACCTGCGTATCTCTCGGGCCGCCCTTCC

CGAGGGGCTCCCCGAGGCCTCCCGCCTTCACCGGGCTCTGTTCCGGCTGT

CCCCGACGGCGTCAAGGTCGTGGGACGTGACACGACCGCTGCGGCGTCAG

CTCAGCCTTGCAAGACCCCAGGCGCCCGCGCTGCACCTGCGACTGTCGCC

GCCGCCGTCGCAGTCGGACCAACTGCTGGCAGAATCTTCGTCCGCACGGC

CCCAGCTGGAGTTGCACTTGCGGCCGCAAGCCGCCAGGGGGCGCCGCAGA

GCGCGTGCGCGCAACGGGGACCACTGTCCGCTCGGGCCCGGGCGTTGCTG

CCGTCTGCACACGGTCCGCGCGTCGCTGGAAGACCTGGGCTGGGCCGATT

GGGTGCTGTCGCCACGGGAGGTGCAAGTGACCATGTGCATCGGCGCGTGC

CCGAGCCAGTTCCGGGCGGCAAACATGCACGCGCAGATCAAGACGAGCCT

GCACCGCCTGAAGCCCGACACGGTGCCAGCGCCCTGCTGCGTGCCCGCCA

GCTACAATCCCATGGTGCTCATTCAAAAGACCGACACCGGGGTGTCGCTC

CAGACCTATGATGACTTGTTAGCCAAAGACTGCCACTGCATATGA.
```

The amino acid sequence of murine GDF15 following cleavage of the 32 residue signal sequence is (shown with an optional N-terminal methionine codon in parentheses):

```
                                     (SEQ ID NO: 8)
(M)SQGDALAMPEQRPSGPESQLNADELRGRFQDLLSRLHANQSREDSNS

EPSPDPAVRILSPEVRLGSHGQLLLRVNRASLSQGLPEAYRVHRALLLLT

PTARPWDITRPLKRALSLRGPRAPALRLRLTPPPDLAMLPSGGTQLELRL

RVAAGRGRRSAHAHPRDSCPLGPGRCCHLETVQATLEDLGWSDWVLSPRQ
```

-continued
```
LQLSMCVGECPHLYRSANTHAQIKARLHGLQPDKVPAPCCVPSSYTPVVL

MHRTDSGVSLQTYDDLVARGCHCA
``` and is encoded by the DNA sequence (shown with an optional N-terminal methionine codon in parentheses, and optional stop codon):

```
                                     (SEQ ID NO: 7)
(ATG)TCGCAGGGGGACGCCCTGGCAATGCCTGAACAGCGACCCTCCGGC

CCTGAGTCCCAACTCAACGCCGACGAGCTACGGGGTCGCTTCCAGGACCT

GCTGAGCCGGCTGCATGCCAACCAGAGCCGAGAGGACTCGAACTCAGAAC

CAAGTCCTGACCCAGCTGTCCGGATACTCAGTCCAGAGGTGAGATTGGGG

TCCCACGGCCAGCTGCTACTCCGCGTCAACCGGGCGTCGCTGAGTCAGGG

TCTCCCCGAAGCCTACCGCGTGCACCGAGCGCTGCTCCTGCTGACGCCGA

CGGCCCGCCCCTGGGACATCACTAGGCCCCTGAAGCGTGCGCTCAGCCTC

CGGGGACCCCGTGCTCCCGCATTACGCCTGCGCCTGACGCCGCCTCCGGA

CCTGGCTATGCTGCCCTCTGGCGGCACGCAGCTGGAACTGCGCTTACGGG

TAGCCGCCGGCAGGGGCGCCGAAGCGCGCATGCGCACCCAAGAGACTCG

TGCCCACTGGGTCCGGGGCGCTGCTGTCACTTGGAGACTGTGCAGGCAAC

TCTTGAAGACTTGGGCTGGAGCGACTGGGTGCTGTCCCCGCGCCAGCTGC

AGCTGAGCATGTGCGTGGGCGAGTGTCCCCACCTGTATCGCTCCGCGAAC

ACGCATGCGCAGATCAAAGCACGCCTGCATGGCCTGCAGCCTGACAAGGT

GCCTGCCCCGTGCTGTGTCCCCTCCAGCTACACCCCGGTGGTTCTTATGC

ACAGGACAGACAGTGGTGTGTCACTGCAGACTTATGATGACCTGGTGGCC

CGGGGCTGCCACTGCGCTTGA.
```

The amino acid sequence of the recombinant active form of the human GDF15, which comprises a homodimer comprising nine intermolecular disulfide bonds (shown with an optional N-terminal methionine residue in parentheses), is:

```
                                    (SEQ ID NO: 10)
(M)ARNGDHCPLGPGRCCRLHTVRASLEDLGWADWVLSPREVQVTMCIGA

CPSQFRAANMHAQIKTSLHRLKPDTVPAPCCVPASYNPMVLIQKTDTGVS

LQTYDDLLAKDCHCI
``` and is encoded by the DNA sequence (shown with an optional N-terminal methionine codon in parentheses, and optional stop codon):

```
                                     (SEQ ID NO: 9)
(ATG)GCGCGCAACGGGGACCACTGTCCGCTCGGGCCCGGGCGTTGCTGC

CGTCTGCACACGGTCCGCGCGTCGCTGGAAGACCTGGGCTGGGCCGATTG

GGTGCTGTCGCCACGGGAGGTGCAAGTGACCATGTGCATCGGCGCGTGCC

CGAGCCAGTTCCGGGCGGCAAACATGCACGCGCAGATCAAGACGAGCCTG

CACCGCCTGAAGCCCGACACGGTGCCAGCGCCCTGCTGCGTGCCCGCCAG

CTACAATCCCATGGTGCTCATTCAAAAGACCGACACCGGGGTGTCGCTCC

AGACCTATGATGACTTGTTAGCCAAAGACTGCCACTGCATATAA.
```

The amino acid sequence of the recombinant active form of the murine GDF15, which comprises a homodimer comprising nine intermolecular disulfide bonds (shown with an optional N-terminal methionine codon in parentheses), is:

(SEQ ID NO: 12)
(M)SAHAHPRDSCPLGPGRCCHLETVQATLEDLGWSDWVLSPRQLQLSMC

VGECPHLYRSANTHAQIKARLHGLQPDKVPAPCCVPSSYTPVVLMHRTDS

GVSLQTYDDLVARGCHCA and is encoded by the DNA sequence (shown with an optional N-terminal methionine codon in parentheses, and optional stop codon):

(SEQ ID NO: 11)
(ATG)AGCGCGCATGCGCACCCAAGAGACTCGTGCCCACTGGGTCCGGGG

CGCTGCTGTCACCTGGAGACTGTGCAGGCAACTCTTGAAGACTTGGGCTG

GAGCGACTGGGTGTTGTCCCCGCGCCAGCTGCAGCTGAGCATGTGCGTGG

GCGAGTGTCCCCACCTGTATCGCTCCGCGAACACGCATGCGCAGATCAAA

GCACGCCTGCATGGCCTGCAGCCTGACAAGGTGCCTGCCCCGTGCTGTGT

CCCCTCCAGCTACACCCCGGTGGTTCTTATGCACAGGACAGACAGTGGTG

TGTCACTGCAGACTTATGATGACCTGGTGGCCCGGGGCTGCCACTGCGCT

TGA.

As stated herein, the term "GDF15 polypeptide" refers to a GDF polypeptide comprising the human amino acid sequences SEQ ID NOs:2, 6 and 10. The term "GDF15 polypeptide," however, also encompasses polypeptides comprising an amino acid sequence that differs from the amino acid sequence of a naturally occurring GDF polypeptide sequence, e.g., SEQ ID NOs:2, 6 and 10, by one or more amino acids, such that the sequence is at least 85% identical to SEQ ID NOs:2, 6 and 10. GDF polypeptides can be generated by introducing one or more amino acid substitutions, either conservative or non-conservative and using naturally or non-naturally occurring amino acids, at particular positions of the GDF15 polypeptide.

A "conservative amino acid substitution" can involve a substitution of a native amino acid residue (i.e., a residue found in a given position of the wild-type FGF21 polypeptide sequence) with a non-native residue (i.e., a residue that is not found in that same position of the wild-type FGF21 polypeptide sequence) such that there is little or no effect on the polarity or charge of the amino acid residue at that position. Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues can be divided into classes based on common side chain properties:
(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Additional groups of amino acids can also be formulated using the principles described in, e.g., Creighton (1984) PROTEINS: STRUCTURE AND MOLECULAR PROPERTIES (2d Ed. 1993), W.H. Freeman and Company. In some instances it can be useful to further characterize substitutions based on two or more of such features (e.g., substitution with a "small polar" residue, such as a Thr residue, can represent a highly conservative substitution in an appropriate context).

Conservative substitutions can involve the exchange of a member of one of these classes for another member of the same class. Non-conservative substitutions can involve the exchange of a member of one of these classes for a member from another class.

Synthetic, rare, or modified amino acid residues having known similar physiochemical properties to those of an above-described grouping can be used as a "conservative" substitute for a particular amino acid residue in a sequence. For example, a D-Arg residue may serve as a substitute for a typical L-Arg residue. It also can be the case that a particular substitution can be described in terms of two or more of the above described classes (e.g., a substitution with a small and hydrophobic residue means substituting one amino acid with a residue(s) that is found in both of the above-described classes or other synthetic, rare, or modified residues that are known in the art to have similar physiochemical properties to such residues meeting both definitions).

Nucleic acid sequences encoding a GDF15 polypeptide provided herein, including those degenerate to SEQ ID NOs:1, 5 and 9, and those encoding polypeptide variants of SEQ ID NOs:2, 6 and 10 form other aspects of the instant disclosure.

II.B. GDF15 Vectors

In order to express the GDF15 nucleic acid sequences provided herein, the appropriate coding sequences, e.g., SEQ ID NOs:1, 5 or 9, can be cloned into a suitable vector and after introduction in a suitable host, the sequence can be expressed to produce the encoded polypeptide according to standard cloning and expression techniques, which are known in the art (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989). The invention also relates to such vectors comprising a nucleic acid sequence according to the invention.

A "vector" refers to a delivery vehicle that (a) promotes the expression of a polypeptide-encoding nucleic acid sequence; (b) promotes the production of the polypeptide therefrom; (c) promotes the transfection/transformation of target cells therewith; (d) promotes the replication of the nucleic acid sequence; (e) promotes stability of the nucleic acid; (f) promotes detection of the nucleic acid and/or transformed/transfected cells; and/or (g) otherwise imparts advantageous biological and/or physiochemical function to the polypeptide-encoding nucleic acid. A vector can be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

A recombinant expression vector can be designed for expression of a GDF15 protein in prokaryotic (e.g., *E. coli*) or eukaryotic cells (e.g., insect cells, using baculovirus expression vectors, yeast cells, or mammalian cells). Representative host cells include those typically used for cloning and expression, including *Escherichia coli* strains TOP10F', TOP10, DH10B, DH5a, HB101, W3110, BL21 (DE3) and BL21 (DE3)pLysS, BLUESCRIPT (Stratagene), mammalian cell lines CHO, CHO-K1, HEK293, 293-EBNA pIN vectors (Van Heeke & Schuster, *J. Biol. Chem.* 264: 5503-5509 (1989); pET vectors (Novagen, Madison Wis.). Alternatively, the recombinant expression vector can be transcribed and translated in vitro, for example using T7 promoter regulatory sequences and T7 polymerase and an in vitro translation system. Preferably, the vector contains a promoter upstream of the cloning site containing the nucleic acid sequence encoding the polypeptide. Examples of promoters, which can be switched on and off, include the lac promoter, the T7 promoter, the trc promoter, the tac promoter and the tip promoter.

Thus, provided herein are vectors comprising a nucleic acid sequence encoding GDF15 that facilitate the expression of recombinant GDF15. In various embodiments, the vectors comprise an operably linked nucleotide sequence which regulates the expression of GDF15. A vector can comprise or be associated with any suitable promoter, enhancer, and other expression-facilitating elements. Examples of such elements include strong expression promoters (e.g., a human CMV IE promoter/enhancer, an RSV promoter, SV40 promoter, SL3-3 promoter, MMTV promoter, or HIV LTR promoter, EF1alpha promoter, CAG promoter), effective poly (A) termination sequences, an origin of replication for plasmid product in *E. coli*, an antibiotic resistance gene as a selectable marker, and/or a convenient cloning site (e.g., a polylinker). Vectors also can comprise an inducible promoter as opposed to a constitutive promoter such as CMV IE. In one aspect, a nucleic acid comprising a sequence encoding a GDF15 polypeptide which is operatively linked to a tissue specific promoter which promotes expression of the sequence in a metabolically-relevant tissue, such as liver or pancreatic tissue is provided.

II.C. Host Cells

In another aspect of the instant disclosure, host cells comprising the GDF15 nucleic acids and vectors disclosed herein are provided. In various embodiments, the vector or nucleic acid is integrated into the host cell genome, which in other embodiments the vector or nucleic acid is extrachromosomal.

Recombinant cells, such as yeast, bacterial (e.g., *E. coli*), and mammalian cells (e.g., immortalized mammalian cells) comprising such a nucleic acid, vector, or combinations of either or both thereof are provided. In various embodiments cells comprising a non-integrated nucleic acid, such as a plasmid, cosmid, phagemid, or linear expression element, which comprises a sequence coding for expression of a GDF15 polypeptide, are provided.

A vector comprising a nucleic acid sequence encoding a GDF15 polypeptide provided herein can be introduced into a host cell by transformation or by transfection. Methods of transforming a cell with an expression vector are well known.

A GDF15-encoding nucleic acid can be positioned in and/or delivered to a host cell or host animal via a viral vector. Any suitable viral vector can be used in this capacity. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a GDF15 polypeptide-encoding nucleic acid. A viral particle viral vector can comprise a wild-type viral particle or a modified viral particle. The viral vector can be a vector which requires the presence of another vector or wild-type virus for replication and/or expression (e.g., a viral vector can be a helper-dependent virus), such as an adenoviral vector amplicon. Typically, such viral vectors consist of a wild-type viral particle, or a viral particle modified in its protein and/or nucleic acid content to increase transgene capacity or aid in transfection and/or expression of the nucleic acid (examples of such vectors include the herpes virus/AAV amplicons). Typically, a viral vector is similar to and/or derived from a virus that normally infects humans. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

II.D. Isolation of a GDF15 Polypeptide

A GDF15 polypeptide expressed as described herein can be isolated using standard protein purification methods. A GDF15 polypeptide can be isolated from a cell in which is it naturally expressed or it can be isolated from a cell that has been engineered to express GDF15, for example a cell that does not naturally express GDF15.

Protein purification methods that can be employed to isolate a GDF15 polypeptide, as well as associated materials and reagents, are known in the art. Exemplary methods of purifying a GDF15 polypeptide are provided in the Examples herein below. Additional purification methods that may be useful for isolating a GDF15 polypeptide can be found in references such as Bootcov M R, 1997, *Proc. Natl. Acad. Sci. USA* 94:11514-9, Fairlic W D, 2000, *Gene* 254: 67-76.

III. Pharmaceutical Compositions Comprising a GDF15 Polypeptide

Pharmaceutical compositions comprising a GDF15 polypeptide are provided. Such GDF15 polypeptide pharmaceutical compositions can comprise a therapeutically effective amount of a GDF15 polypeptide in admixture with a pharmaceutically or physiologically acceptable formulation agent selected for suitability with the mode of administration. The term "pharmaceutically acceptable carrier" or "physiologically acceptable carrier" as used herein refers to one or more formulation agents suitable for accomplishing or enhancing the delivery of a GDF15 polypeptide into the body of a human or non-human subject. The term includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In some cases it will be preferable to include isotonic agents, for example, sugars, polyalcohols such as mannitol, sorbitol, or sodium chloride in a pharmaceutical composition. Pharmaceutically acceptable substances such as wetting or minor amounts of auxiliary substances such as wetting or emulsifying agents, preservatives or buffers, which enhance the shelf life or effectiveness of the GDF15 polypeptide can also act as, or form a component of, a carrier. Acceptable pharmaceutically acceptable carriers are preferably nontoxic to recipients at the dosages and concentrations employed.

A pharmaceutical composition can contain formulation agent(s) for modifying, maintaining, or preserving, for example, the pH, osmolarity, viscosity, clarity, color, isotonicity, odor, sterility, stability, rate of dissolution or release, adsorption, or penetration of the composition. Suitable formulation agents include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as Polysorbate 20 or Polysorbate 80; Triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON: THE SCIENCE AND PRACTICE OF PHARMACY, 19th edition, (1995); Berge et al., J. Pharm. Sci., 6661), 1-19 (1977). Additional relevant principles, methods, and agents are described in, e.g., Lieberman et al., PHARMACEUTICAL DOSAGE FORMS-DISPERSE SYSTEMS (2nd ed., vol. 3, 1998); Ansel et al., PHARMACEUTICAL DOSAGE FORMS & DRUG DELIVERY SYSTEMS (7th ed. 2000); Martindale, THE EXTRA PHARMACOPEIA (31st edition), Remington's PHARMACEUTICAL SCIENCES (16th-20$^{th}$ and subsequent editions); The Pharmacological Basis Of Therapeutics, Goodman and Gilman, Eds. (9th ed.-1996); Wilson and Gisvolds' TEXTBOOK OF ORGANIC MEDICINAL AND PHARMACEUTICAL CHEMISTRY, Delgado and Remers, Eds. (10th ed., 1998). Principles of formulating pharmaceutically acceptable compositions also are described in, e.g., Aulton, PHARMACEUTICS: THE SCIENCE OF DOSAGE FORM DESIGN, Churchill Livingstone (New York) (1988), EXTEMPORANEOUS ORAL LIQUID DOSAGE PREPARATIONS, CSHP (1998), incorporated herein by reference for any purpose).

The optimal pharmaceutical composition will be determined by a skilled artisan depending upon, for example, the intended route of administration, delivery format, and desired dosage (see, e.g., Remington's PHARMACEUTICAL SCIENCES, supra). Such compositions can influence the physical state, stability, rate of in vivo release, and rate of in vivo clearance of the a GDF15 polypeptide.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the present invention, FGF21 polypeptide mutant compositions can be prepared for storage by mixing the selected composition having the desired degree of purity with optional formulation agents (Remington's PHARMACEUTICAL SCIENCES, supra) in the form of a lyophilized cake or an aqueous solution. Furthermore, the GDF15 polypeptide product can be formulated as a lyophilizate using appropriate excipients such as sucrose.

The GDF15 polypeptide pharmaceutical compositions can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising the desired GDF15 polypeptide in a pharmaceutically acceptable vehicle. A particularly suitable vehicle for parenteral injection is sterile distilled water in which a GDF15 polypeptide is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a GDF15 polypeptide can be formulated as a dry powder for inhalation. GDF15 polypeptide inhalation solutions can also be formulated with a propellant for aerosol delivery. In yet another embodiment, solutions can be nebulized. Pulmonary administration is further described in International Publication No. WO 94/20069, which describes the pulmonary delivery of chemically modified proteins.

It is also contemplated that certain formulations can be administered orally. In one embodiment of the present invention, GDF15 polypeptides that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the GDF15 polypeptide. Diluents, flavorings, low melting point waxes, vegetable oils, lubricants, suspending agents, tablet disintegrating agents, and binders can also be employed.

Another pharmaceutical composition can involve an effective quantity of a GDF15 polypeptide in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional GDF15 polypeptide pharmaceutical compositions will be evident to those skilled in the art, including formulations involving GDF15 polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO 93/15722, which describes the controlled release of porous polymeric microparticles for the delivery of pharmaceutical compositions, and Wischke & Schwendeman, 2008, *Int. J. Pharm.* 364: 298-327, and Freiberg & Zhu, 2004, *Int. J. Pharm.* 282: 1-18, which discuss microsphere/microparticle preparation and use). As described herein, a hydrogel is an example of a sustained- or controlled-delivery formulation.

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et al., 1983, *Biopolymers* 22: 547-56), poly(2-hydroxyethyl-methacrylate) (Langer et al., 1981, *J. Biomed. Mater. Res.* 15: 167-277 and Langer, 1982, *Chem. Tech.* 12: 98-105), ethylene vinyl acetate (Langer et al., supra) or poly-D(-)-3-hydroxybutyric acid (European Patent No. 0 133 988). Sustained-release compositions can also include liposomes, which can be prepared by any of several methods known in the art. See, e.g., Epstein et al., 1985, Proc. Natl. Acad. Sci. U.S.A. 82: 3688-92; and European Patent Nos. 0 036 676, 0 088 046, and 0 143 949.

A GDF15 polypeptide pharmaceutical composition to be used for in vivo administration typically should be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In a specific embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

The effective amount of a GDF15 polypeptide pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which a GDF15 polypeptide is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg; or 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, up to about 100 mg/kg. In yet other embodiments, the dosage can be 50 µg/kg, 100 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 100 µg/kg, 200 µg/kg, 300 µg/kg, 400 µg/kg, 500 µg/kg, 600 µg/kg, 700 µg/kg, 800 µg/kg, 900 µg/kg, 1000 µg/kg, 2000 µg/kg, 3000 µg/kg, 4000 µg/kg, 5000 µg/kg, 6000 µg/kg, 7000 µg/kg, 8000 µg/kg, 9000 µg/kg or 10 mg/kg.

The frequency of dosing will depend upon the pharmacokinetic parameters of the GDF15 polypeptide in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

In order to deliver drug, e.g., a GDF15 polypeptide, at a predetermined rate such that the drug concentration can be maintained at a desired therapeutically effective level over an extended period, a variety of different approaches can be employed. In one example, a hydrogel comprising a polymer such as a gelatin (e.g., bovine gelatin, human gelatin, or gelatin from another source) or a naturally-occurring or a synthetically generated polymer can be employed. Any percentage of polymer (e.g., gelatin) can be employed in a hydrogel, such as 5, 10, 15 or 20%. The selection of an appropriate concentration can depend on a variety of factors, such as the therapeutic profile desired and the pharmacokinetic profile of the therapeutic molecule.

Examples of polymers that can be incorporated into a hydrogel include polyethylene glycol ("PEG"), polyethylene oxide, polyethylene oxide-co-polypropylene oxide, co-polyethylene oxide block or random copolymers, polyvinyl alcohol, poly(vinyl pyrrolidinone), poly(amino acids), dextran, heparin, polysaccharides, polyethers and the like.

Another factor that can be considered when generating a hydrogel formulation is the degree of crosslinking in the hydrogel and the crosslinking agent. In one embodiment, cross-linking can be achieved via a methacrylation reaction involving methacrylic anhydride. In some situations, a high degree of cross-linking may be desirable while in other situations a lower degree of crosslinking is preferred. In some cases a higher degree of crosslinking provides a longer sustained release. A higher degree of crosslinking may provide a firmer hydrogel and a longer period over which drug is delivered.

Any ratio of polymer to crosslinking agent (e.g., methacrylic anhydride) can be employed to generate a hydrogel with desired properties. For example, the ratio of polymer to crosslinker can be, e.g., 8:1, 16:1, 24:1, or 32:1. For example, when the hydrogel polymer is gelatin and the crosslinker is methacrylate, ratios of 8:1, 16:1, 24:1, or 32:1 methyacrylic anhydride:gelatin can be employed.

V. Therapeutic Uses of GDF15 Proteins and Nucleic Acids

GDF15 polypeptides can be used to treat, diagnose or ameliorate, a metabolic condition or disorder. In one embodiment, the metabolic disorder to be treated is diabetes, e.g., type 2 diabetes mellitus. In another embodiment, the metabolic condition or disorder is obesity. In other embodiments the metabolic condition or disorder is dyslipidemia, elevated glucose levels, elevated insulin levels or diabetic nephropathy. For example, a metabolic condition or disorder that can be treated or ameliorated using a GDF15 polypeptide includes a state in which a human subject has a fasting blood glucose level of 100 mg/dL or greater, for example 125, 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL. Conditions that can be treated using a pharmaceutical composition comprising a GDF15 polypeptide can also be found in the relevant literature, e.g., American Diabetes Association Standards of Medical Care in Diabetes Care-2011, American Diabetes Association, Diabetes Care Vol. 34, No. Supplement 1, S11-S61, 2010, incorporated herein by reference.

In application, a metabolic disorder or condition, such as Type 2 diabetes, elevated glucose levels, elevated insulin levels, dyslipidemia, obesity or diabetic nephropathy, can be treated by administering a therapeutically effective dose of a GDF15 polypeptide, e.g., a human GDF15 polypeptide such as SEQ ID NOs:2, 6 or 10, to a patient in need thereof. The administration can be performed as described herein, such as by IV injection, intraperitoneal (IP) injection, subcutaneous injection, intramuscular injection, or orally in the form of a tablet or liquid formation. In some situations, a therapeutically effective or preferred dose of a GDF15 polypeptide can be determined by a clinician. A therapeutically effective dose of GDF15 polypeptide will depend, inter alia, upon the administration schedule, the unit dose of agent administered, whether the GDF15 polypeptide is administered in combination with other therapeutic agents, the immune status and the health of the recipient. The term "therapeutically effective dose," as used herein, means an amount of GDF15 polypeptide that elicits a biological or medicinal response in a tissue system, animal, or human being sought by a researcher, medical doctor, or other clinician, which includes alleviation or amelioration of the symptoms of the disease or disorder being treated, i.e., an amount of a GDF15 polypeptide that supports an observable level of one or more desired biological or medicinal response, for example lowering blood glucose, insulin, triglyceride, or cholesterol levels; reducing body weight; or improving glucose tolerance, energy expenditure, or insulin sensitivity.

It is noted that a therapeutically effective dose of a GDF15 polypeptide can also vary with the desired result. Thus, for example, in situations in which a lower level of blood glucose is indicated a dose of GDF15 will be correspondingly higher than a dose in which a comparatively lower level of blood glucose is desired. Conversely, in situations in which a higher level of blood glucose is indicated a dose of GDF15 will be correspondingly lower than a dose in which a comparatively higher level of blood glucose is desired.

In various embodiments, a subject is a human having a blood glucose level of 100 mg/dL or greater can be treated with a GDF15 polypeptide.

In one embodiment, a method of the instant disclosure comprises first measuring a baseline level of one or more metabolically-relevant compounds such as glucose, insulin, cholesterol, lipid in a subject. A pharmaceutical composition comprising a GDF15 polypeptide is then administered to the subject. After a desired period of time, the level of the one or more metabolically-relevant compounds (e.g., blood glucose, insulin, cholesterol, lipid) in the subject is again measured. The two levels can then be compared in order to determine the relative change in the metabolically-relevant compound in the subject. Depending on the outcome of that comparison another dose of the pharmaceutical composition comprising a GDF15 molecule can be administered to achieve a desired level of one or more metabolically-relevant compound.

It is noted that a pharmaceutical composition comprising a GDF15 polypeptide can be co-administered with another compound. The identity and properties of compound co-administered with the GDF15 polypeptide will depend on the nature of the condition to be treated or ameliorated. A non-limiting list of examples of compounds that can be administered in combination with a pharmaceutical composition comprising a GDF15 polypeptide include rosiglitizone, pioglitizone, repaglinide, nateglitinide, metformin, exenatide, stiagliptin, pramlintide, glipizide, glimeprirideacarbose, and miglitol.

VI. Kits

Also provided are kits for practicing the disclosed methods. Such kits can comprise a pharmaceutical composition such as those described herein, including nucleic acids encoding the peptides or proteins provided herein, vectors and cells comprising such nucleic acids, and pharmaceutical compositions comprising such nucleic acid-containing compounds, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of a GDF15 polypeptide; and (b) one or more containers for the pharmaceutical composition. Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, obesity, type 2 diabetes, dyslipidemia or diabetic nephropathy.

Instructions can be printed on a substrate, such as paper or plastic, etc, and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded.

Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

EXAMPLES

The following examples, including the experiments conducted and results achieved, are provided for illustrative purposes only and are not to be construed as limiting the present invention.

Example 1

Preparation of GDF15 Polypeptides

E. coli that were transformed with a GDF 15 expression vector constructed with an affinity tag were grown to an optical density of 9 at 600 nm and then induced and harvested at an optical density of 63 by centrifugation 6 hours later. Frozen cell paste was thawed and re-suspended into buffer at 15% (wt./vol.) with a low shear homogenizer until the slurry was homogeneous. The cells were then subjected to high shear homogenization to break open and release product-containing inclusion bodies. The resulting homogenate was then centrifuged at 5,000×g for an hour at 5 C to harvest the inclusion bodies as a pellet, leaving the cytoplasmic contaminants in the discarded supernatant. The residual cytoplasm is washed from the inclusion bodies by homogeneously re-suspending the pellet to the original homogenate volume using chilled water and a low shear homogenizer followed by centrifugation as before. The resulting pellet, washed inclusion bodies (WIBS), is then frozen at −80 C.

A sufficient amount of WIBS and guanidine hydrochloride (GnHCl) was used at pH 8.5 in a reducing-solubilization to result in approximately 25 mg/ml reduced product and 6 M GnHCl final concentrations. The solubilization was then rapidly diluted 25-fold with stirring into a refolding buffer containing redox reagents, chaotrope and co-solvents at alkaline pH. The refold solution was allowed to gently stir and air oxidize at 6 C for 72 hours or until the solution was negative to Ellman's reagent. The refold solution at 5 C was then clarified by depth filtration to allow for a 10-fold ultra-filtration concentration and subsequent diafiltration into a buffer containing 50 mM sodium phosphate and low chaotrope concentration at pH 8.5. The subsequent retentate was warmed to 25 C and then the pH lowered into the acidic range to cause precipitation of contaminants. The precipitate was removed by centrifugation at 5,000×g for 30 min at 25 C and the resulting supernatant further clarified by 0.45 um filtration. The filtrate (AP) was then adjusted to pH 8.5, and low salt concentration to permit the first step of purification involving immobilized metal affinity chromatography (IMAC).

Following protein folding and AP, the GDF 15 was purified using a two-step chromatography train. The adjusted AP was applied to an IMAC column that is equilibrated with buffered chaotrope containing a low salt concentration at pH 8.5. The column was next washed with equilibration buffer until a baseline ultraviolet (UV) level is obtained. Product and contaminants are eluted by step-wise increases in displacer concentration and the elutions were collected and subsequently assayed by Coomasie-stained SDS-PAGE (sodium dodecyl sulfate polyacrylamide gel electrophoresis) to identify which eluate fractions contained a polypeptide that migrates at the predicted molecular weight of GDF 15. After the IMAC was completed, the pooled fraction containing product is adjusted to pH 7.2 and 5 mM EDTA at 25 C. The product was converted into the mature length GDF 15 by adding a low concentration of an enzyme to cleave off the affinity tag at 25 C for several hours. The cleavage reaction mixture was adjusted with an organic modifier and acidic pH by the addition of acetic acid and organic solvent. This allowed for the final chromatography step consisting of a linear gradient elution of product from a reverse phase column conducted at 25 C. The elution from the chromatography was collected as fractions and then assayed by SDS-PAGE to determine the appropriate fractions to pool for homogeneous product. The resulting pool was buffer exchanged by diafiltration into a weakly acidic buffer, concentrated by ultra-filtration, sterile filtered, and stored at 5 C or frozen.

Example 2

Regulation of Murine GDF15 in Liver and Epidydimal Tissue

Liver and fat tissues are major metabolic organs in mammalians. To identify potential novel therapeutic targets for treatment of metabolic disorders, a microarray study was conducted to compare gene expression patterns in liver and fat tissues of fed or fasted wildtype or obese ob/ob mice. Liver or epidydimal fat tissues were harvested for RNA extraction from age-matched C57B16 or ob/ob male mice (Jackson Labs) that had free access to food ("fed") or that were fasted for 24 hr ("fast").cRNA samples were hybridized to custom made micro array chips (Agilent). Data was analyzed to compare gene expression patterns between wildtype and ob/ob mice and between fed and fasted mice. Murine GDF15 (SEQ ID NO:4; NCBI Accession Number BC067248.1) was identified as a target gene regulated by feeding/fasting in liver and fat tissues as well as differentially expressed in wildtype and ob/ob mice.

FIGS. 1A and 1B shows the change of signal intensity of GDF15 in liver and fat tissues, respectively. It is noted that GDF15 expression levels are significantly higher in liver tissues from ob/ob mice than C57B1/6 mice. GDF15 expression levels were observed to be downregulated by fasting in liver in both C57B1/6 mice and ob/ob mice. GDF15 expression levels were also significantly higher in fat tissues from ob/ob mice than C57B1/6 mice. Fasting increased GDF15 gene expression levels in both C57B1/6 mice and ob/ob mice. However, the fold induction was less robust in ob/ob mice. These data suggest that GDF15 may be a novel metabolic regulator.

Example 3

Induction of GDF15 by PPAR Agonists

PPARα is nuclear receptor regulating metabolism in liver and a major therapeutic target for metabolic disorders. PPARα is reported to be the master regulator mediating fasting-induced FGF21 upregulation in liver (Inagaki T 2007 *Cell Metab* 5:415-25). Male C57B16 mice (Jackson) were treated with a PPARα agonist clofibrate (500 mg/kg), and liver tissues were harvested 1 day after treatment for RNA extraction. cRNA samples were hybridized to mouse 10K micro array (Motorola). Data was analyzed to identify PPARα target genes in mouse liver. FIG. 2A shows that GDF15 expression was largely induced by clofibrate treatment in mouse liver and demonstrates that GDF15 is a downstream target gene of PPARα in liver.

PPARγ is a master regulator of gene expression in the fat tissue and PPARγ agonists are clinically approved or being developed for diabetes treatment. Some PPARγ target genes, such as adiponectin, an adipokine and a PPARγ target gene in the fat tissue (Maeda N 2001 *Diabetes* 50:2094-9), are also considered as therapeutic targets for treatment of type 2 diabetes. Gene expression patterns in 3T3-L1 adipocytes treated with vehicle or PPARγ agonist BRL49653 were compared, and murine GDF15 was identified as a target gene inducible PPARγ agonist treatment in adipocytes. Differentiated 3T3-L1 adipocytes were treated with 10 uM BRL49653 for 24 hours. RNA samples were isolated and cRNA samples were hybridized to mouse 10K micro array (Motorola). Data was analyzed to identify PPARγ genes in 3T3-L1 adipocytes. FIG. 2B shows that GDF15 expression was largely induced by BRL49653 treatment in 3T3-L1 mouse adipocytes and demonstrates that GDF15 is a downstream target gene of PPARγ in adipocytes, suggesting that GDF15 has the potential to be a therapeutic target for diabetes treatment.

Example 4

Murine GDF15 Reduces Food Intake, Body Weight Gain, Blood Insulin Levels, Blood Glucose Levels and Blood Lipid Levels in Ob/Ob Mice Since GDF15 was robustly regulated by metabolic changes or pharmacological treatments that activate major pathways regulating metabolism, we examined if overexpression of GDF15 in vivo would cause metabolic phenotypes in obese and diabetic ob/ob mice (Coleman D L 1973 *Diabetologia* 9:287-93). Adeno-associated virus (AAV) was used to achieve in vivo overexpression for two major advantages. First, unlike transgene, AAV can be applied to adult animals and does not interfere with fetal development. Secondly, unlike other types of virus used for in vivo gene overexpression, AAV produced with helper-free system is replication-defective and is not pathogenic (Matsushita T 1998 *Gene Therapy* 5: 938-45). muGDF15 full-length cDNA (SEQ ID NO:3) was cloned into AAV vector with EF1a promoter and bGH polyA. AAVs were produced with helper-free system and purified by chromatography and gradient centrifugation. Seven-week-old male ob/ob mice (Jackson Labs) were injected with $8 \times 10^{12}$ genomic copy/animal AAV-muGDF15 or control virus through the tail vein.

Figure 3:
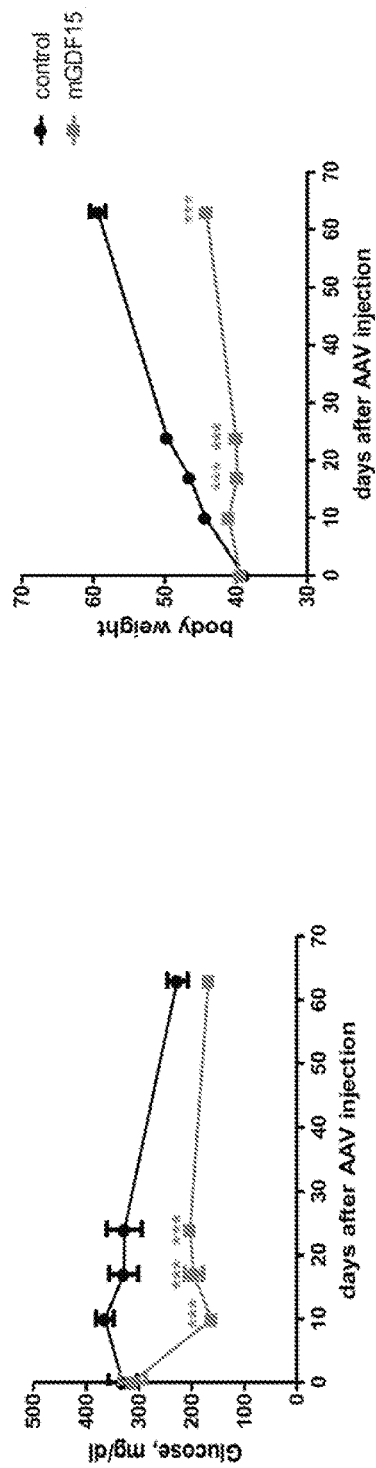
FIG. 3 is a series of plots and bar graphs showing the improvement in the metabolic profile of leptin-deficient ob/ob mice following AAV-mediated treatment with murine GDF15; the effect of AAV murine GDF15 injection on plasma glucose levels (FIG. 3A) and body weight (FIG. 3C) were measured for two months. Plasma insulin levels were measured two weeks after AAV injection (FIG. 3B) and average daily food intake was measured three weeks after AAV injection (FIG. 3D). Total cholesterol (FIG. 3E), NEFA (FIG. 3F), triglyceride (FIG. 3G) and insulin levels (FIG. 3H) were measured two months after AAV injection.
Figure 3:
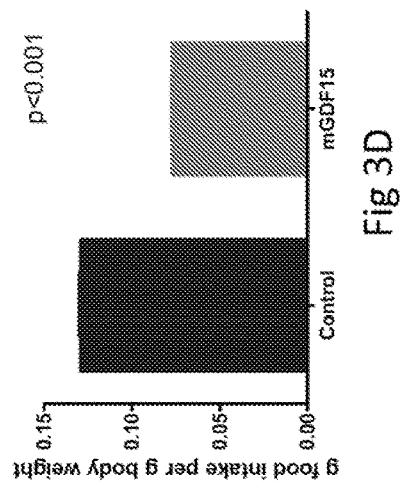
Figure 3:
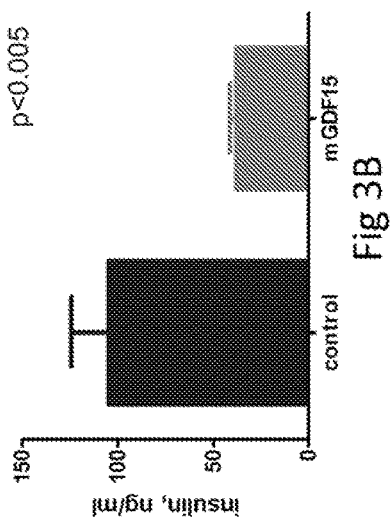
Figure 3:
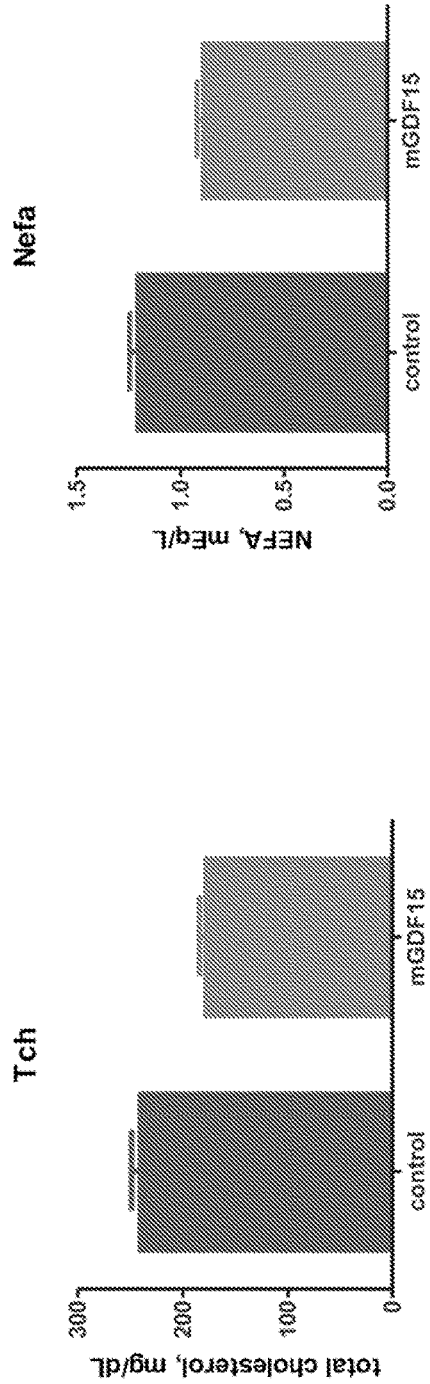
Figure 3:
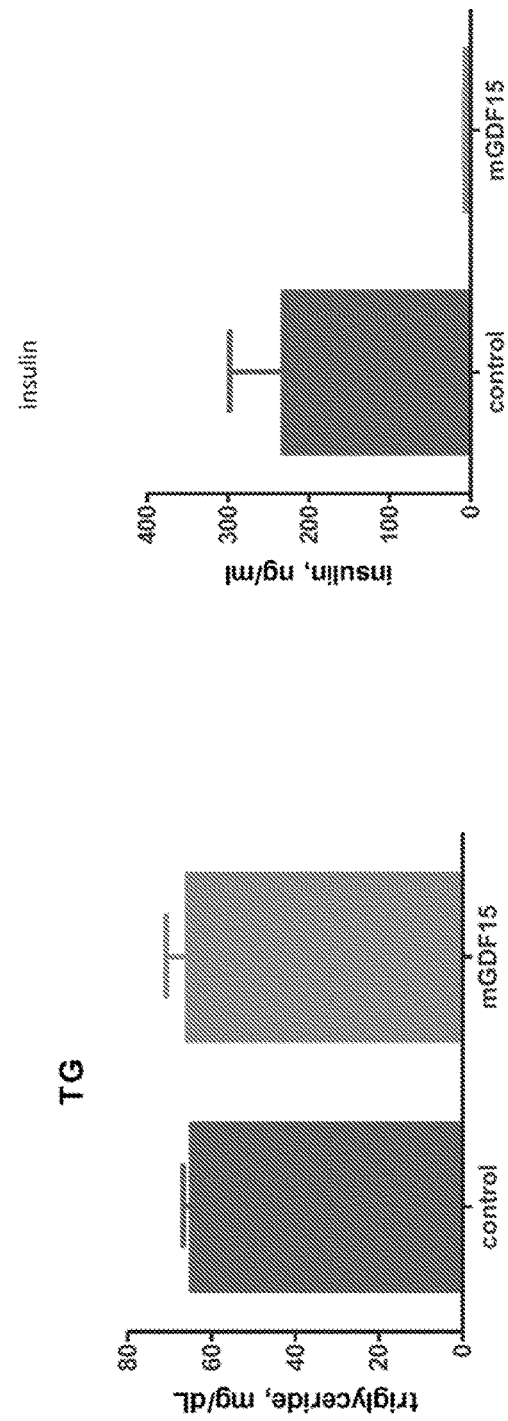

Glucose levels and body weight were examined on days 10, 17, 24, and 63 (FIGS. 3A and 3C, respectively). Food intake was measured weekly from day 3 to day 24 (FIG. 3D). Blood insulin was also measured on day 17 (FIG. 3B). Total cholesterol (FIG. 3E), free fatty acids (FIG. 3F), triglyceride (FIG. 3G), and insulin levels (FIG. 3H) were measured on day 63.

The lowered body weight, food intake, blood glucose, insulin, triglyceride and cholesterol levels in AAV-muGDF15 group compared to control virus treated group demonstrated that AAV mediated in vivo overexpression of muGDF15 largely corrected metabolic abnormalities in ob/ob mice, including hyperphagia, obesity, hyperglycemia, hyperinsulinemia and dyslipidemia. This data confirmed our hypothesis that GDF15 regulates body metabolism and can be a potential therapeutic target for the treatment of a metabolic disorder, such as obesity, diabetes and dyslipidemia.

Example 5

Murine GDF15 Improves Hyperglycemia in Ob/Ob Mice, Independent of Reduction of Food Intake and Without Body Weight Gain GDF15 significantly reduced excessive food intake and body weight gain in ob/ob mice, raising the question whether the improvement of hyperglycemia is secondary to the lowered food intake and reduced body weight gain. A pair-feeding study was performed to determine whether GDF15 could improve hyperglycemia independently from reduced food intake and without body weight gain. Seven-week old male ob/ob mice (Jackson Labs) were injected with $8 \times 10^{12}$ genomic copy/animal AAV-muGDF15 or a control virus through the tail vein as described in Example 4.

Figure 4:
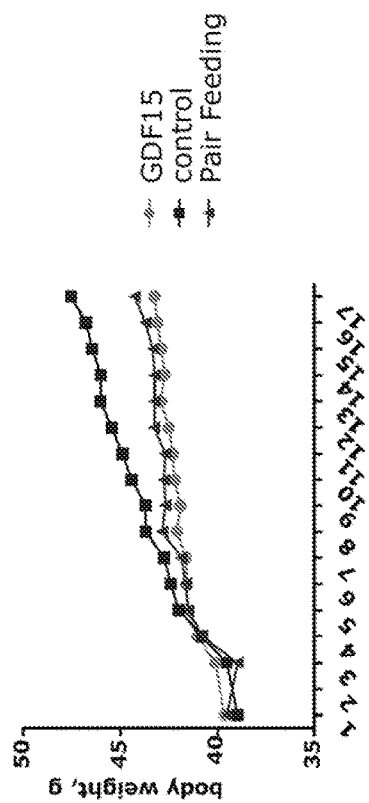
FIG. 4 is a series of two plots and two bar graphs showing the glucose lowering activity of AAV-mediated treatment of ob/ob mice with murine GDF15 and demonstrating that the glucose lowering effect is independent of reduced body weight. The pair-feeding study includes 3 groups of animals; one group injected with control AVV and had free access to food, a second group injected with AAV GDF15 and had free access to food, and a third group injected with control AVV was fed the same amount of food that was consumed by the group of animals injected with GDF15 AAV on the previous day. The ratio of food intake to body weight over time in mice injected with GDF15 or control AAV is shown in FIG. 4A.
Figure 4:
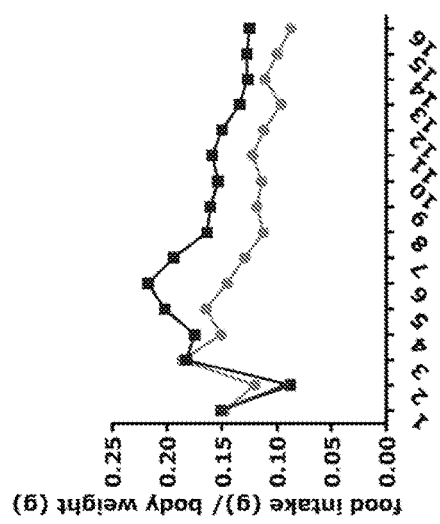
Figure 4:
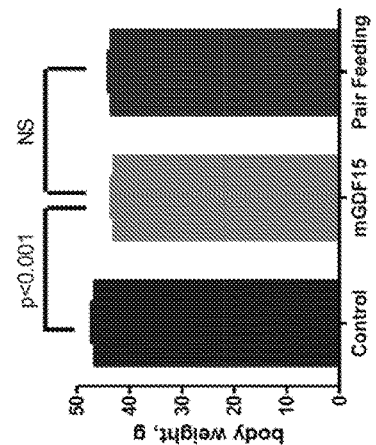
Figure 4:
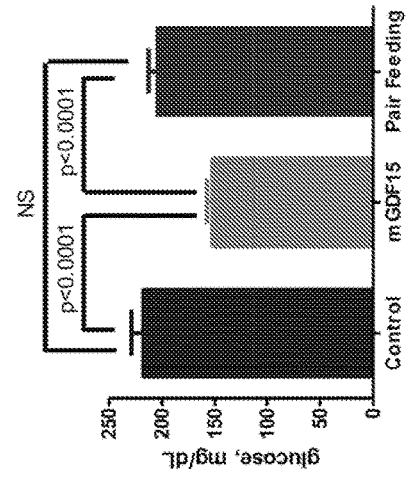

One group of control virus-injected mice (pair-feeding group) had limited food access. The amount of food given to the pair-feeding group (grams food intake/grams body weight) was calculated to be equal to the amount of food consumed by AAV-muGDF15 injected mice the day before (grams food intake/grams body weight), after normalized by body weight. Body weight and food intake were monitored daily, and the effect of GDF15 on these parameters is shown in FIGS. 4A and 4B, respectively. Glucose levels and body weight were measured at the end of the study and the effect of GDF15 on these parameters is shown in FIGS. 4C and 4D, respectively.

Through the course of the 17-day pair-feeding study, the GDF15 group had reduced food intake and body weight gain compared to control virus group, and the pair-fed group maintained similar body weight to the GDF15 group (FIGS. 4A and 4B). However, GDF15 group had significantly lower glucose levels than both the control group and the pair-fed group, suggesting that GDF15 can improve glucose management in hyperglycemic ob/ob mice independently of food intake or body weight.

Example 6

The Efficacy of Murine GDF15 is More Robust in a High-Fat Diet Induced Obesity (DIO) Model Than in a Normal Chow-Fed Model We next examined the efficacy of AAV mediated GDF15 overexpression in B6D2F1 mice on high fat diet, another rodent model to examine efficacy of diabetic therapeutics (Karasawa H 2009 *Metab Clin Exp* 58:296-33). For comparison, mice fed normal chow were also included in the study. Four-week-old male B6D2F1 mice (Harlan Labs) were put on 60% high fat diet or normal chow for 3 weeks. They were subsequently injected with $8 \times 10^{12}$ genomic copy/ms AAV-muGDF 15 or a control virus through tail vein as described in Example 4.

Figure 5:
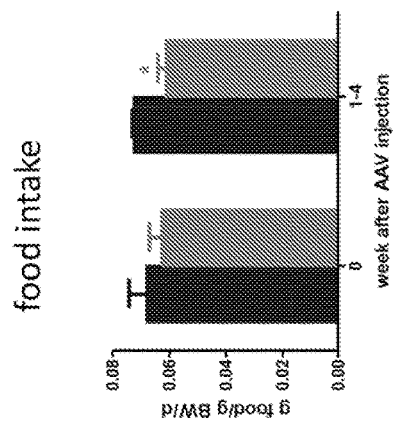
FIG. 5 is a series of four plots and two bar graphs showing the effects of murine GDF15 AAV on plasma glucose levels, body weight and food intake, respectively in mice fed a high fat diet (FIGS. 5A-5C) and the same thing in mice fed a normal chow diet (FIGS. 5D-5F).
Figure 5:
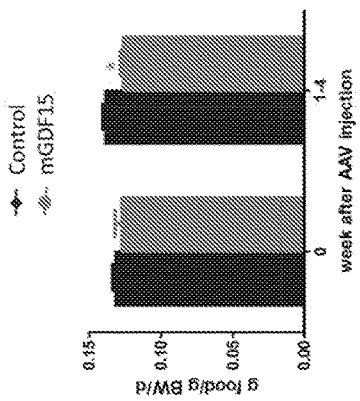
Figure 5:
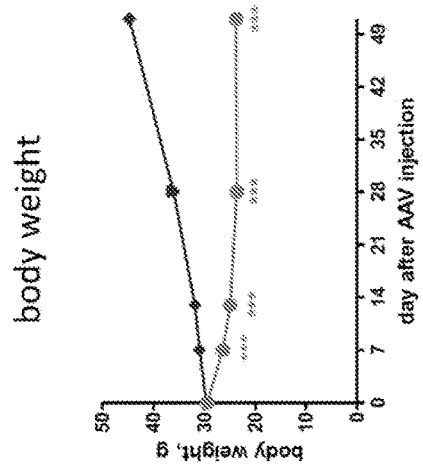
Figure 5:
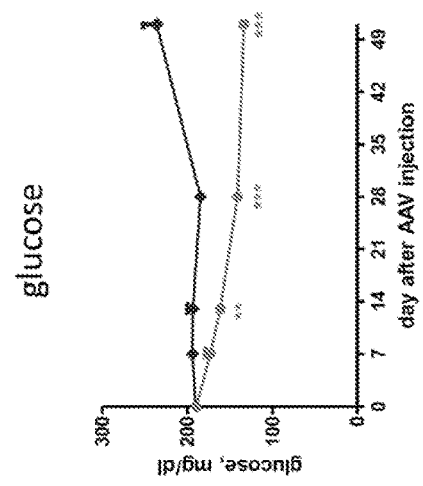
Figure 5:
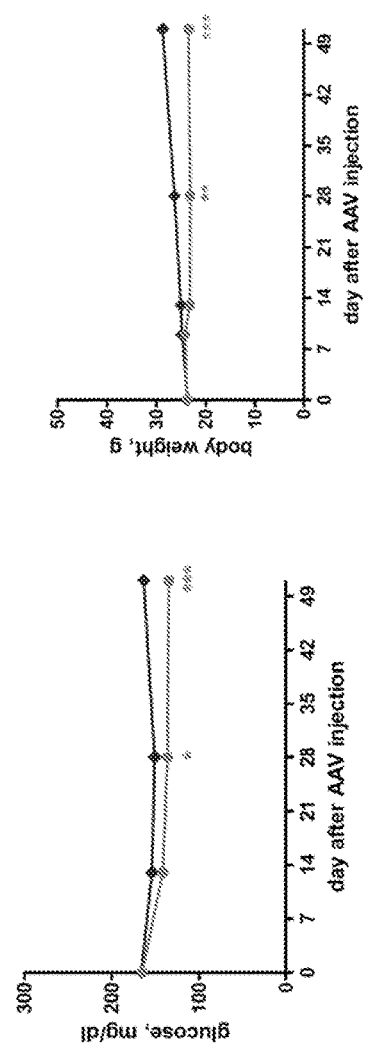

Glucose levels and body weight were measured on days 7, 13 and 28 by glucometer; the results are shown in FIGS. 5A and 5B, respectively. Food intake was measured weekly for four weeks and the results are shown in FIG. 5C. The results for the control animals fed a normal chow diet are shown in FIGS. 5D-5F. AAV-muGDF15 largely decreased blood glucose levels and body weight in mice on high fat diet. On contrary, in mice on regular chow of normal blood glucose levels, the effect was very mild.

These results indicate that GDF15 is a metabolic regulator that takes effect selectively in the disease model, and will likely not cause hypoglycemia, unlike some diabetes therapies.

Example 7

Murine GDF15 Improves Insulin Sensitivity and Glucose Tolerance in DIO Mice

Diabetes is a metabolic disease of insulin resistance and insulin insufficiency. To further understand the potential of GDF15 for diabetes treatment, we tested glucose tolerance and insulin sensitivity in mice fed high fat diet treated that had been administered with AAV-muGDF15 or control virus. Male B6D2F1 mice (Harlan Labs) were fed a 60% high fat diet for three weeks and then injected with $8 \times 10^{12}$ genomic copy/animal AAV-muGDF15 or control virus through the tail vein as described in Example 4.

Figure 6:
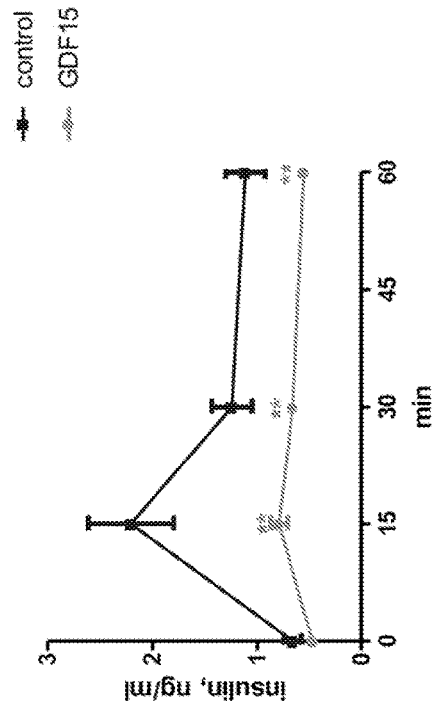
FIG. 6 is a series of four plots showing the effect of AAV-mediated treatment with murine GDF15 on insulin sensitivity and glucose tolerance in mice fed a high fat diet.
Figure 6:
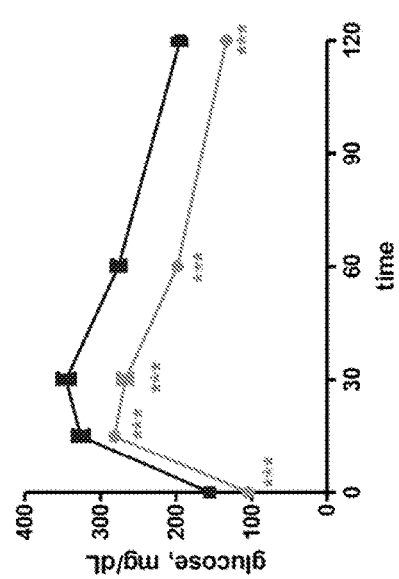
Figure 6:
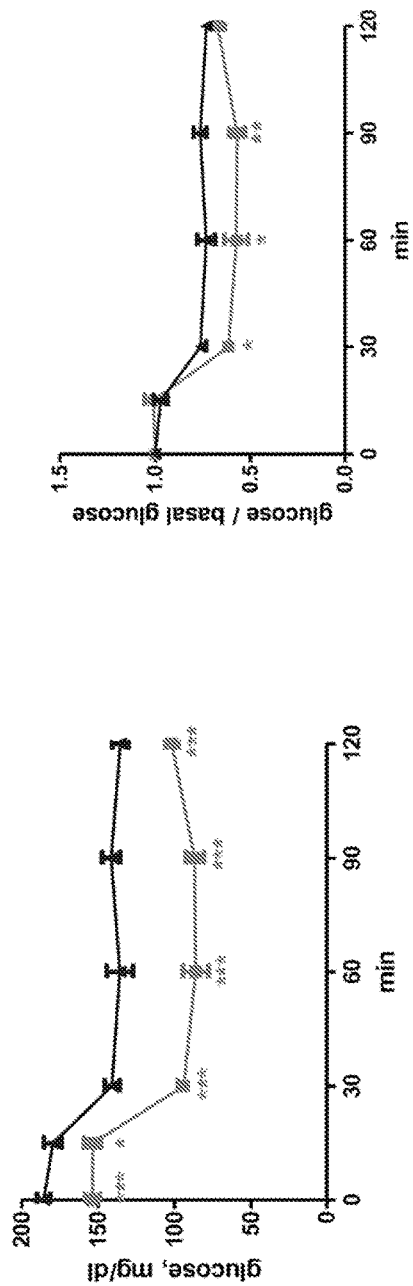

A glucose tolerance test (GTT) was performed three weeks after the AAV injection. The GTT was performed as follows: animals were fasted for 4 hours. Following a measurement of body weight and glucose levels (by glucometer) and bleeding for insulin measurement, a 20% glucose solution in water was orally administered at 10 ml/kg. Glucose levels at 15, 30, 60, 120 min after glucose dosing were measured by glucometer. Blood samples were collected at 15, 30, 60 min for measurement of serum insulin levels. FIGS. 6A and 6B show the glucose curve and insulin curve during the GTT, respectively. In the GTT study, the GDF15 group had lower glucose levels at all time points compared to control group (FIG. 6A), indicating that GDF15 treated animals have improved glucose tolerance. The glucose-induced insulin secretion (GSIS) was also lower at all time points (FIG. 6B), indicating that less insulin was required for glucose disposal after the oral glucose load, which suggests GDF15 treatment improved insulin sensitivity in these mice.

To directly test insulin sensitivity in these mice, an insulin sensitivity test (IST) was performed two weeks after AAV injection on 4 hr fasted mice; i.p. dosing of 0.5 u/kg insulin was used. The insulin sensitivity test (IST) was performed as follows—animals were fasted for 4 hours. Following measurement of body weight and glucose levels by glucometer, animals were i.p. dosed with 10 ml/kg of 0.5 u/10 ml Novolin solution. Glucose levels at 15, 30, 60, 120 min after glucose dosing were measured by glucometer. FIG. 6C shows the glucose curve during IST. The GDF15 treated group had lower glucose at all time points compared to control group. FIG. 6D shows the glucose levels normalized to basal glucose, and GDF15 treated group had lower glucose/basal glucose ratio at 30, 60, 90 min compared to control group, strongly indicating improved insulin sensitivity in GDF15 treated animals.

Example 8

Human GDF15 Improves Glucose Tolerance in DIO Mice

Mouse GDF15 mature peptide and human GDF15 mature peptide share 68.7% homology. To examine whether human GDF15 is functional in mouse models, glucose tolerance was tested in B6D2F1 DIO mice treated with AAV-huGDF15 or control virus. Male B6D2F1 mice (Harlan Labs) were put on 60% high fat diet for five months, then injected with $8 \times 10^{12}$ genomic copy/animal AAV-huGDF15 or control virus through tail vein as described in Example 4.

Figure 7:
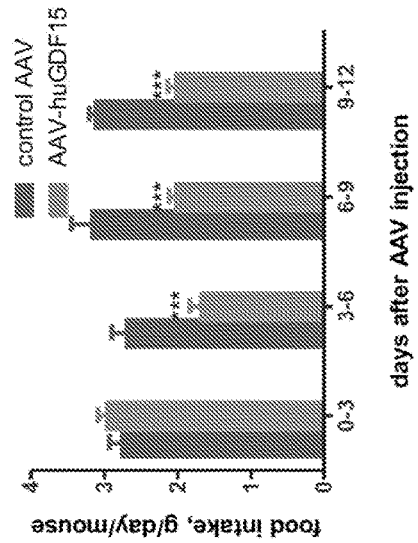
FIG. 7 is a series of a plot and four bar graphs showing the effect of AAV-mediated human GDF15 treatment of DIO mice on glucose levels (FIG. 7A); food intake (FIG. 7B); body weight (FIG. 7C); and the amount of human GDF15 expressed in DIO mice (FIG. 7D).
Figure 7:
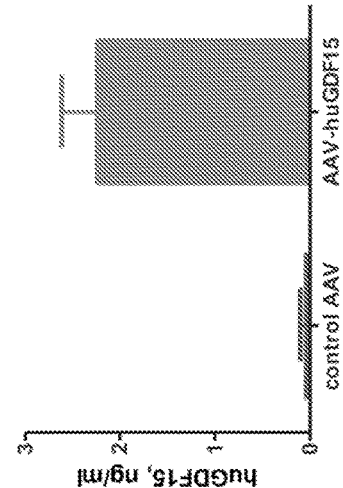
Figure 7:
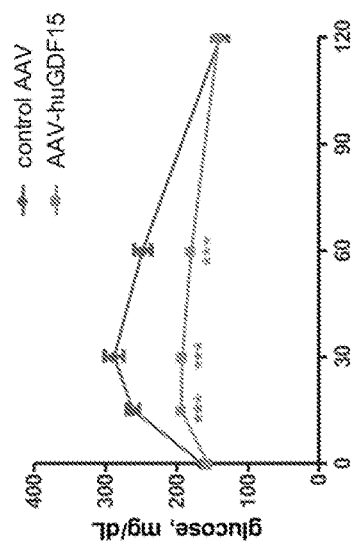
Figure 7:
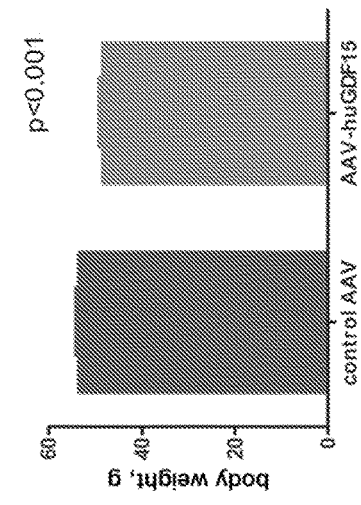

A glucose tolerance test was performed as described in Example 7 two weeks after AAV injection with 4 hour fasted mice; a 2 g/kg oral glucose challenge was used. FIG. 7A depicts the results of the GTT. Food intake was measured every three days for 12 days. FIG. 7B shows the results of the food intake measurement over the 12 day period.

Body weight was measured before the glucose tolerance test was performed, at the two week timepoint. FIG. 7C depicts the results of the body weight measurements at the two week timepoint.

Finally, plasma GDF15 levels at the two week time point were measured by huGDF 15 ELISA (R&D systems). FIG. 7D shows the amount of huGDF 15 detected. The circulating GDF15 levels in rodent are not clear due to lack of detection method. In normal humans, circulating GDF15 levels are reported to be several hundred pg/ml (Moore AG, 2000 *J Clin Endocrinol Metab* 85: 4781-8). Our data shows that AAV-hGDF15 treated group had several nanograms of huGDF15 in circulation (FIG. 7D).

Collectively, this data demonstrates that similarly to mouse GDF15, human GDF15 is efficacious in mouse models and the function conserved well between the two homologs, even though they only share 68.7% sequence homology.

Example 9

Human GDF15 Prevents Worsening of Insulin Sensitivity and Glucose Tolerance in KK-Ay Mice We further tested the efficacy of GDF15 in KK-Ay mice, an obese-diabetic rodent model with different etiology and symptoms from ob/ob and DIO mice (Iwatsuka H 1970 *Endocrinol Jpn* 17:23-35). Seventeen-week-old male KK.Cg-Ay mice (Jackson Labs) were injected with $8 \times 10^{12}$ genomic copy/animal AAV-huGDF15 or control virus through tail vein as described in Example 4.

A glucose tolerance test was performed on four hour fasted mice at three and at six week timepoints after AAV injection; a 2 g/kg oral glucose challenge was used. The control group became more glucose intolerant at 6 weeks as animals grew older and disease progressed, while GDF15 group maintained similar glucose tolerance 6 weeks and 3 weeks post AAV injection (FIG. 8A), suggesting that GDF15 treatment prevented disease progression in these animals. The body weight and blood insulin levels of the mice were examined before glucose challenge. The effect of the AAV injection on body weight and blood insulin is shown in FIGS. 8B and 8C, respectively. Both control group and GDF15 group were slightly hyperinsulinemic 3 weeks after injection (FIG. 8C). While the control group became more hyperinsulinemic at 6 weeks, GDF15 group showed trend of improved hyperinsulinemia (FIG. 8C), suggesting that similar to what was observed in B6D2F1 high fat diet mice, GDF15 treatment improved glucose tolerance in KK-Ay mice through enhanced insulin sensitivity.

These data implies that GDF15 improves glucose tolerance in all diabetic disease mouse models tested.

Example 10

Human GDF15 Improves Glucosuria and Proteinuria in KKAy Mice

A very well-documented diabetic phenotype in KK-Ay mice is renal complications, including glucosuria and proteinuria (Reddi A S 1988 Adv Exp Med Biol 246: 7-15). We also examined the glucose and albumin excretion in KK-Ay mice after GDF15 treatment. Seventeen-week-old male KK.Cg-Ay mice (Jackson Labs) were injected with $8 \times 10^{12}$ genomic copy/animal AAV-huGDF15 or control virus through tail vein as described in Example 4.

Figure 9:
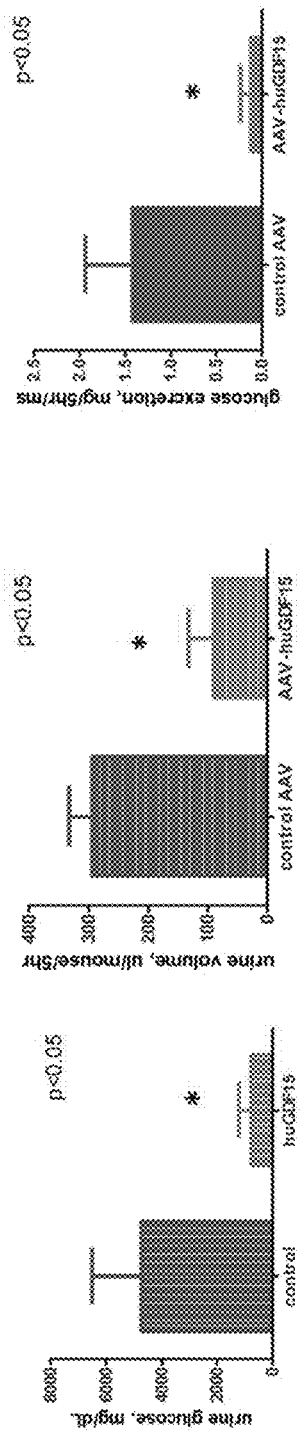
FIG. 9 is a series of nine bar graphs showing the effect of AAV-mediated human GDF15 on glucosuria in KKAy mice over a 3-4 week period.
Figure 9:
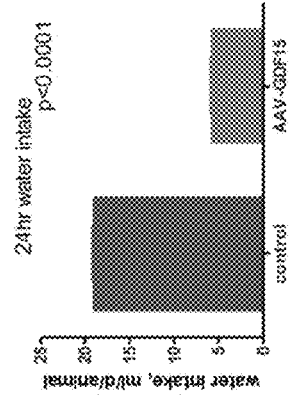
Figure 9:
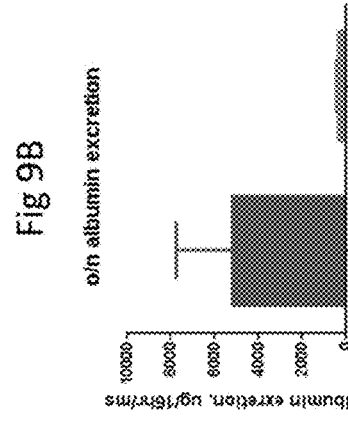
Figure 9:
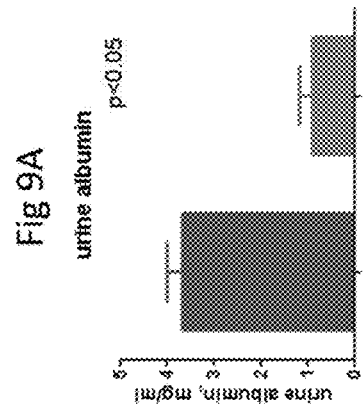
Figure 9:
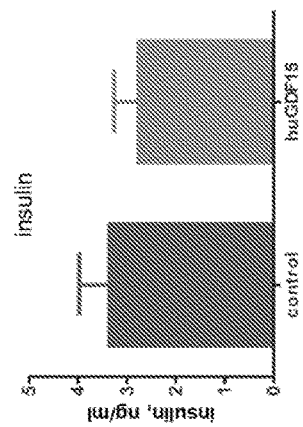
Figure 9:
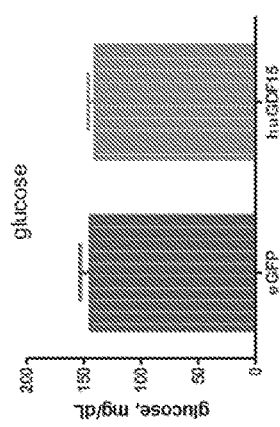
Figure 9:
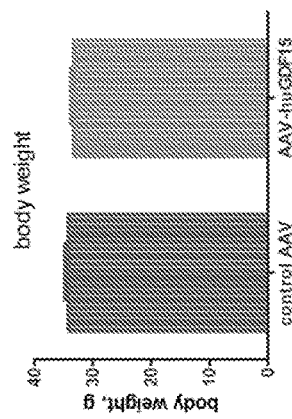
Figure 9:
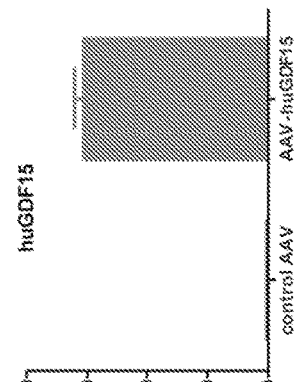
Figure 9:
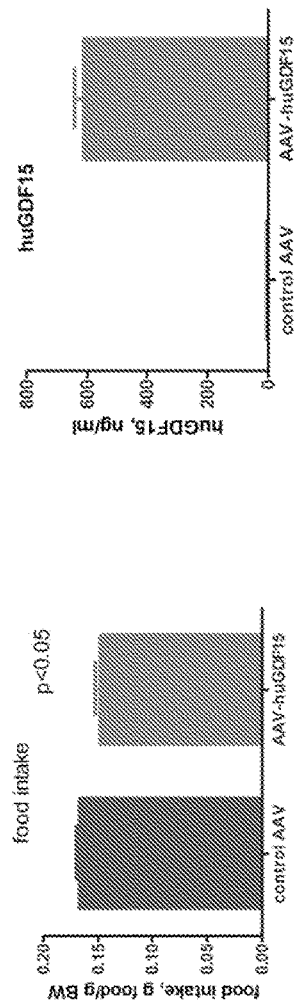

Three weeks after AAV injection, urine glucose levels, urine albumin levels, urine volume, daily water intake, serum insulin levels, blood glucose levels, serum huGDF15 levels, body weight, and food intake were examined. The results are shown in FIGS. 9A-9K (FIG. 9A shows urine glucose levels, 9B shows urine volume, 9C glucose excretion, 9D urine albumin, 9E albumin excretion, 9F water intake, 9G insulin levels, 9H glucose levels, 9I body weight, and 9J food intake, and 9K huGDF15 levels. GDF15 group had significantly improved glucosuria compared with control group, demonstrated with lowering of urine glucose levels (FIG. 9A), urine volume (FIG. 9B) and total glucose excretion (FIG. 9C). Similarly, they also had significantly improved proteinuria, as demonstrated by lowered urine albumin levels (FIG. 9D), urine volume (FIG. 9B) and total urine albumin excretion (FIG. 9E). GDF15 group also reduced water intake to about 6 ml/d/animal, which is similar to water intake of a normal animal, while water intake of control group was about 19 ml/d/animal.

These results indicate that GDF15 significantly improved glucose and albumin excretion in urine and may have additional beneficial effect in diabetic nephropathy.

Example 11

Murine GDF15 Reduces Fat Mass and Fat Mass/Total Body Mass Ratio in a DIO Model

Since GDF15 robustly reduced food intake and body weight gain in ob/ob and B6D2F1 DIO mice, body mass and fat mass were measured in B6D2F1 DIO mice after AAV-muGDF15 injection to determine if GDF15 mainly lowers body fat mass and may be useful as an obesity treatment or mainly lowers body lean mass, which would be undesired. Four-week-old male B6D2F1 mice (Harlan) were put on 60% high fat diet or normal chow for 3 week, then injected with $8 \times 10^{12}$ genomic copy/animal AAV-muGDF15 or control virus through tail vein as described in Example 4.

Figure 10:
FIG. 10 is a series of four bar graphs showing the effect of AAV-mediated murine GDF15 on the total body mass (FIG. 10A); fat mass (FIG. 10B); fat mass/total body mass (FIG. 10C); and non-fat mass/total body mass (FIG. 10D) in DIO mice.
Figure 10:
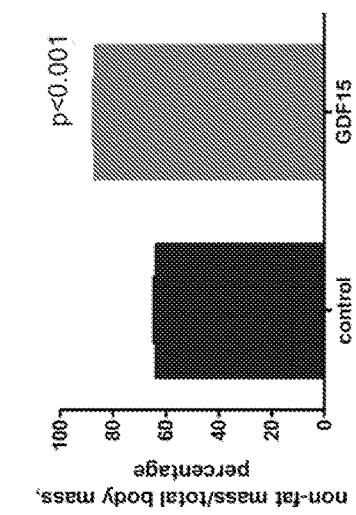
Figure 10:
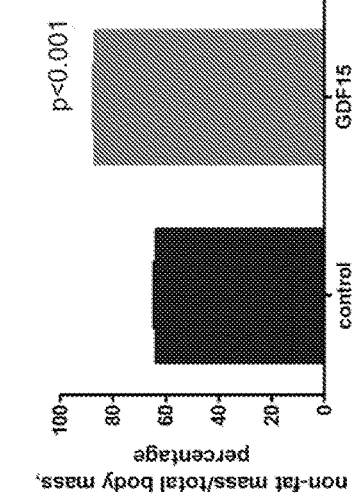
Figure 10:
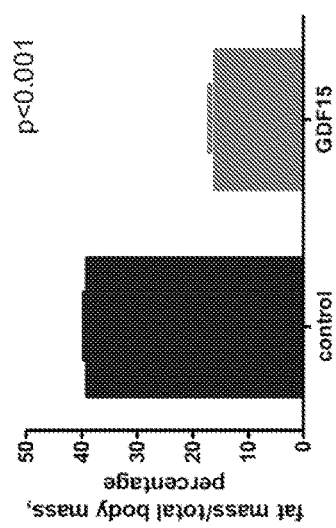

Five months after AAV injection, total body mass and fat mass were measured by DEXA scan (PIXImus II, GE). The results are shown in FIGS. 10A (total body mass) and 10B (fat mass). The ratio of fat mass/total body mass and the ratio of non-fat mass/total mass were also calculated (FIGS. 10C and 10D, respectively). After 5 months, mice on high fat diet with no exposure to exogenous GDF15 (control group) gained much weight and were excessively obese while GDF15 group maintained normal body mass similar to lean and young animals (FIG. 10A). The GDF15 group also had much lower body fat mass (FIG. 10B) and body fat mass/total mass ratio (FIG. 10C). In contrast, non-fat mass/total mass ratio had increased in GDF15 group (FIG. 10D). This data suggests that GDF15 treatment mainly lowers body fat mass and could be considered as a treatment for obesity.

Example 12

Human GDF15 Reduces Fat Mass and Fat Mass/Total Body Mass Ratio in DIO Model

For reasons similar to those outlined in Example 12, body mass and fat mass were measured in B6D2F1 DIO mice after AAV-huGDF15 injection. Male B6D2F1 mice (Harlan Labs) were put on 60% high fat diet for five months, then injected with $8 \times 10^{12}$ genomic copy/animal AAV-huGDF15 or control virus through tail vein as described in Example 4.

Figure 11:
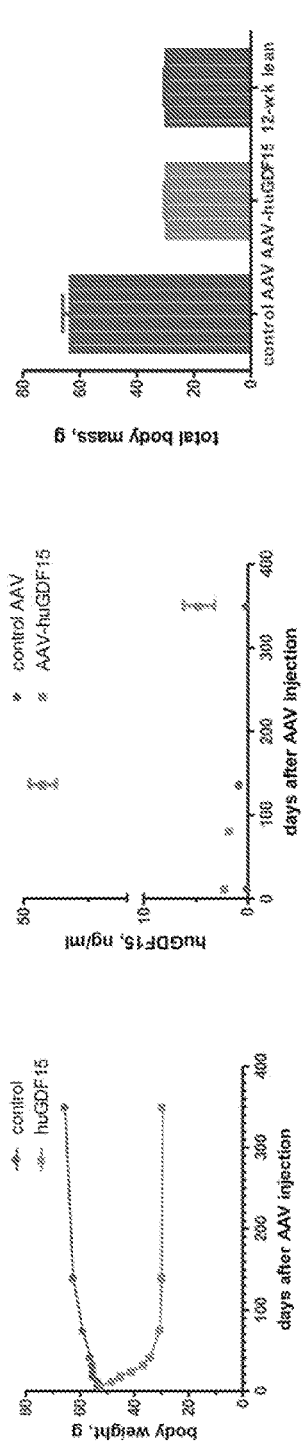
FIG. 11 is a series of two plots and six bar graphs showing the effect of AAV-mediated human GDF15 on DIO mice.
Figure 11:
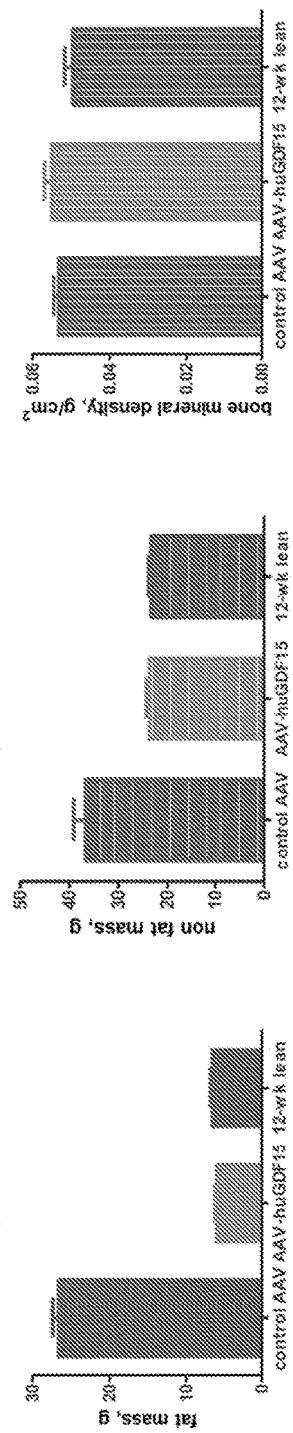
Figure 11:

One year after AAV injection, the body weight of the AAV-hGDF15 treated group was maintained at around 30 g (FIG. 11A), and huGDF15 plasma level was maintained at around 5 ng/ml (FIG. 11B). Total body mass (FIG. 11C), fat mass (FIG. 11D), and bone mineral density (FIG. 11E) were measured by DEXA scan (PIXImus II, GE). The ratio of fat mass/total body mass and the ratio of non-fat mass/total mass ratio were also calculated (FIGS. 11G and 11H, respectively). A group of 12-week-old male B6D2F1 mice on normal chow was included in the DEXA scan for comparison.

This experiment demonstrates that human GDF15 exhibits anti-obesity properties by decreasing fat mass and increasing non-fat mass/total body bass ratio.

Example 13

Recombinant Murine GDF15 Protein Improves Hyperglycemia and Hyperphagia in Leptin-Deficient Ob/Ob Mice We demonstrated strong metabolic efficacy of mouse and human GDF15 in different mouse models through AAV mediated in vivo expression. Next, we tested the efficacy of recombinant mouse GDF15 proteins in ob/ob mice. Six-week-old male ob/ob mice (Jackson Labs) were dosed subcutaneously with 5 mg/kg rmGDF15 protein or vehicle buffer twice per day. Briefly, ob/ob male mice were randomized by food intake, body weight and glucose levels into vehicle and treatment group. Animals were subcutaneously dosed twice daily with 5 mg/kg recombinant muGDF15 protein or vehicle buffer for 2 days.

Figure 12:
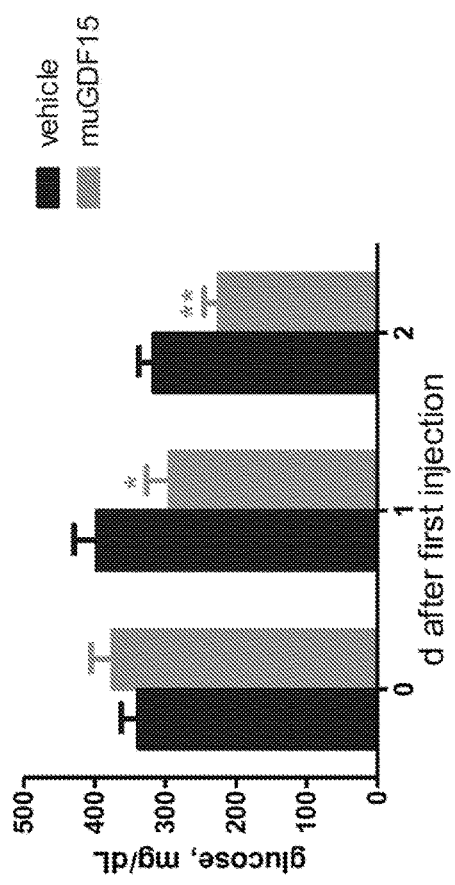
FIG. 12 is a series of three bar graphs showing the effect of recombinant murine GDF15 on glucose and food intake in ob/ob mice.
Figure 12:
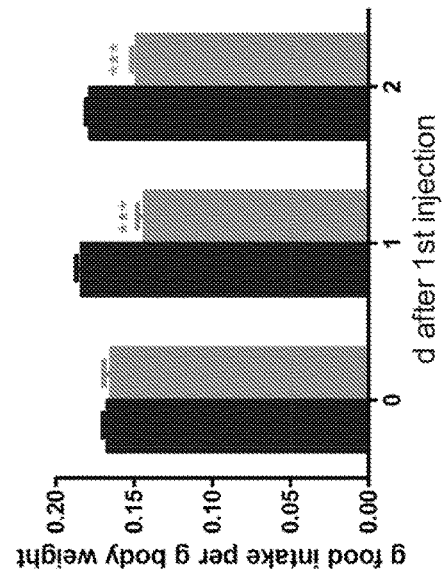
Figure 12:
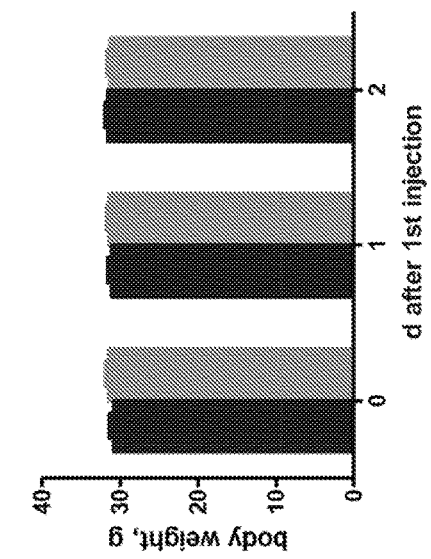

Glucose, body weight, food intake before injection and on days 1 and 2 were measured. For all timepoints, the glucose levels are shown in FIG. 12A, body weight is shown in FIG. 12B and food intake is shown in FIG. 12C.

These results demonstrate that exogenously administered recombinant mouse GDF15 protein is efficacious in ob/ob mice, similar to AAV-muGDF15.

Example 14

Recombinant Human GDF15 Protein Improves Hyperglycemia and Hyperphagia in Leptin-Deficient Ob/Ob Mice The efficacy of recombinant human GDF15 protein was also tested in ob/ob mice. Seven-week-old male ob/ob mice (Jackson Labs) were dosed subcutaneously with 5, 1.5, 0.5, 0.15 mg/kg rhGDF15 protein or vehicle buffer, by single injection. Animals were randomized as described in Example 13.

Figure 13:
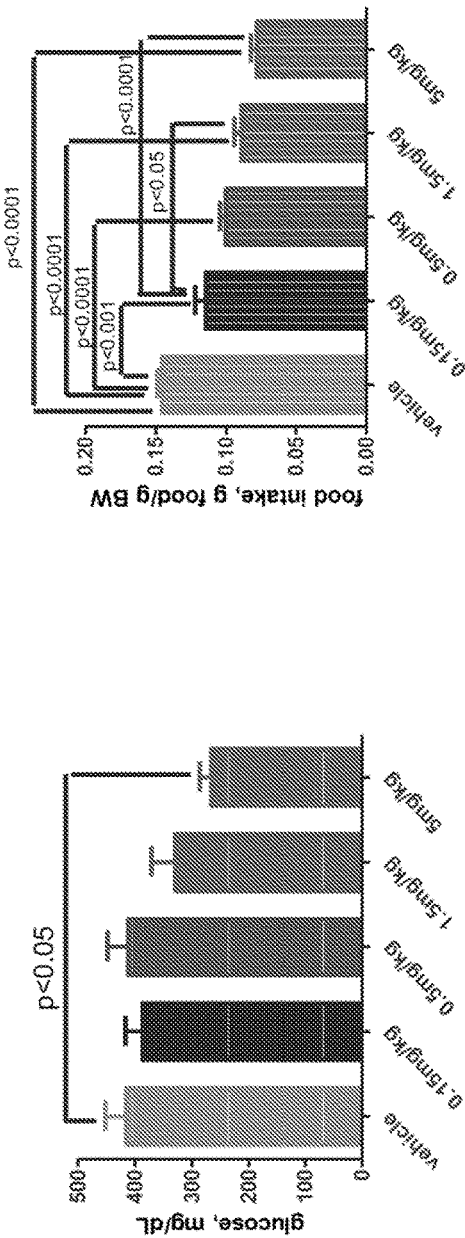
FIG. 13 is a series of three bar graphs showing the effect of recombinant human GDF15 on plasma glucose levels, food intake and body weight in ob/ob mice.
Figure 13:
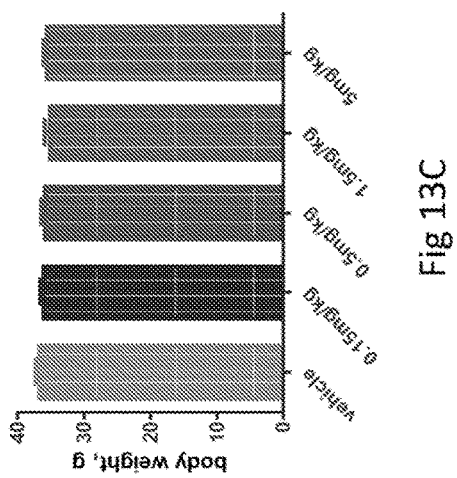

Glucose, body weight, food intake were measured 16-17 hours after treatment. Glucose levels are shown in FIG. 13A, food intake is shown in FIG. 13B and body weight is shown in FIG. 13C.

The data indicates that exogenously administered recombinant human GDF15 protein acutely improves hyperphagia and hyperglycemia in ob/ob mice, and the efficacy was dose-dependent.

Example 15

Recombinant Human GDF15 Protein Improves Glucose Tolerance in DIO Mice

We further tested the efficacy of recombinant human GDF15 protein in DIO model. Male B6D2F1 mice (Harlan Labs) on 60% high fat diet for six months were dosed subcutaneously with 5 mg/kg rhGDF15 protein or vehicle buffer by single dosing, animals were randomized as described in Example 13.

A glucose tolerance test (GTT) was performed three days after dosing on 4 hr fasted mice; a 1 g/kg oral glucose challenge was used. The results of the GTT are shown in FIG. 14A. Food intake was measured daily and is shown in FIG. 14B. Body weight was measured before the GTT was performed and is shown in FIG. 14C.

Collectively these results indicate that recombinant human GDF15 protein is efficacious in a DIO mouse model.

Example 16

Recombinant Human GDF15 Improves Lipid Tolerance

Another interesting metabolic activity of GDF15 we discovered is that GDF15 acutely improves lipid tolerance in mice. Male B6D2F1 mice (Harlan Labs) on 60% high fat diet for two months were dosed subcutaneously with 5 mg/kg rhGDF15 protein or vehicle buffer. Four hours later, mice were orally dosed with 20 ml/kg 20% Intralipid®. Serum triglyceride levels were measured at 0, 60, 90, 120, 180 min after lipid challenge by a colorimetric assay (Sigma). The measured serum triglyceride levels are presented in FIG. 15A. Serum rhGDF15 levels at 180 min were measured by huGDF15 ELISA (R&D Systems) and are shown in FIG. 15B.

Figure 15:
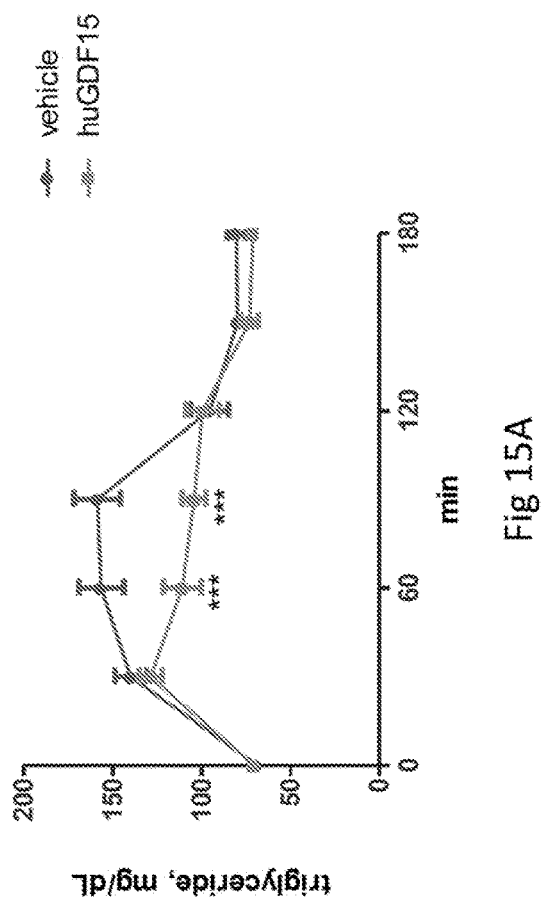
FIG. 15 is a plot and a bar graph showing the effect of recombinant human GDF15 on lipid metabolism in B6D2F1 male mice following an oral lipid challenge.
Figure 15:
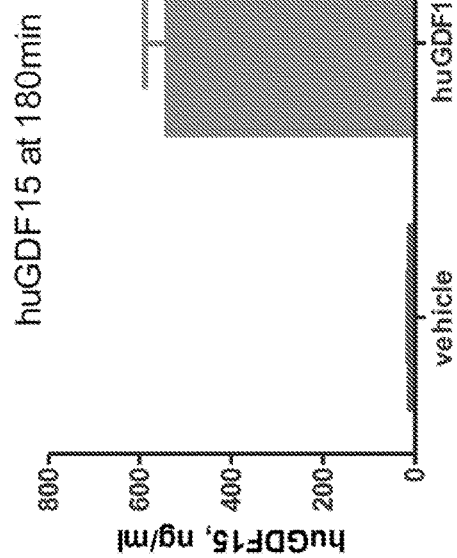

Serum triglyceride levels increased at 30, 60, 90 min after oral intralipid challenge in both GDF15 and vehicle treated animals (FIG. 15A). However, the triglyceride levels at 60 and 90 min were significantly lower in treated group, indicating that GDF15 acutely improved lipid tolerance in these animals (FIG. 15A). Dyslipidemia including hypertriglycerdeamia is a major risk factor for cardiovascular disease, the leading outcome that causes mortality in diabetes patients (Hokanson J E 1996 *J. Cardiovasc. Risk* 3:213-219). The acute improvement of lipid tolerance by GDF15 suggests that GDF15 can provide a beneficial effect in diabetic dyslipidemia, particularly postprandial dyslipidemia.

Example 17

Murine GDF15 Improves the Insulin and Lipid Profile in a DIO Model

Figure 16:
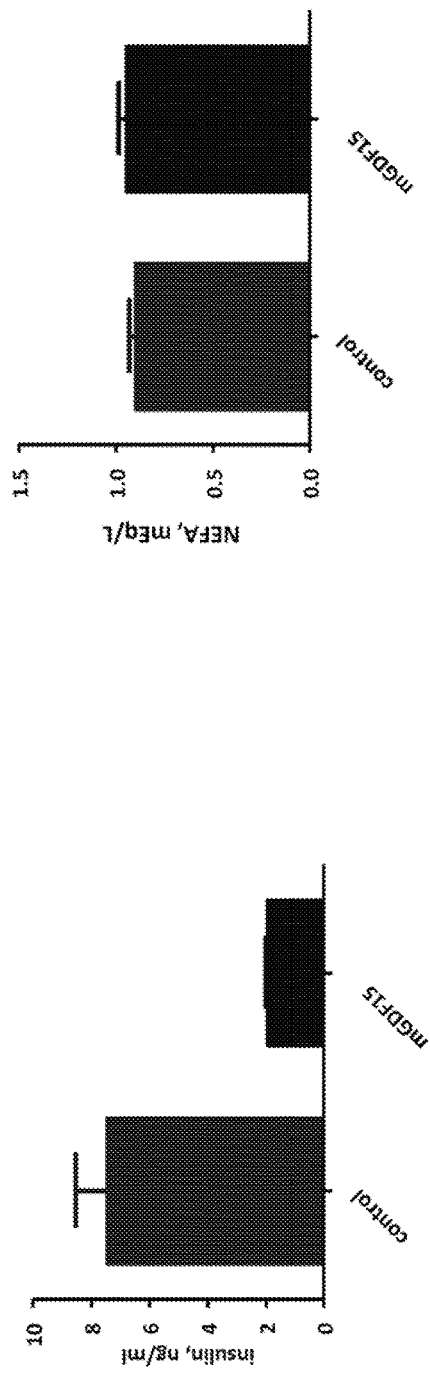
FIG. 16 is a series of four bar graphs showing the blood chemistry of B6D21F mice fed a high-fat diet for three weeks after AAV-mediated murine GDF15 administration.
Figure 16:
Figure 16:
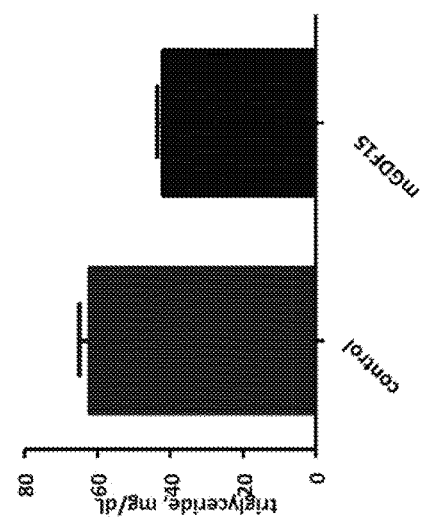

Since GDF15 acutely improves lipid tolerance, we also examined if chronically, GDF15 improves blood lipid profiles. B6D2F1 mice (Harlan Labs) were put on 60% high fat diet and injected with $8 \times 10^{12}$ genomic copy/animal AAV-muGDF15 or control virus through tail vein as described in Example 4. Blood insulin, total cholesterol, NEFA and triglyceride levels were measured 3 weeks after AAV injection. The results are shown in FIG. 16; FIG. 16A shows insulin levels, FIG. 16B NEFA levels, FIG. 16C total cholesterol levels, and FIG. 16D triglyceride levels. GDF15 group had lower cholesterol levels (FIG. 16C) and triglyceride levels compared to control group, demonstrating that GDF15 chronically improves lipid profile. This data further indicates that GDF15 treatment can provide a beneficial effect in diabetic dyslipidemia.

What is claimed is:

1. A method of improving glucose tolerance in a subject comprising administering to a subject in need thereof a therapeutically effective amount of an isolated GDF15 polypeptide, wherein the isolated GDF15 polypeptide consists of the amino acid sequence of SEQ ID NO: 10, wherein the subject has a fasting blood glucose level of greater than or equal to 100 mg/dL, and wherein administration of the GDF15 polypeptide improves glucose tolerance in the subject.

2. The method of claim 1, wherein the subject has type 2 diabetes.

3. The method of claim 1, wherein the subject has dyslipidemia.

4. The method of claim 1, wherein the subject is obese.

5. The method of claim 1, wherein the subject has diabetic nephropathy.

6. The method of claim 1, wherein the subject is a mammal.

7. The method of claim 6, wherein the mammal is a human.

8. The method of claim 1, wherein the GDF15 polypeptide is encoded by a nucleic acid molecule comprising a nucleotide sequence consisting of SEQ ID NO: 9.

9. The method of claim 1, wherein the GDF15 polypeptide is administered in the form of a pharmaceutical composition comprising the GDF15 polypeptide in admixture with a pharmaceutically-acceptable carrier.

10. The method of claim 1, further comprising the step of determining the subject's blood glucose level at a timepoint subsequent to the administration.

11. The method of claim 1, further comprising the step of determining the subject's serum insulin level at a timepoint subsequent to the administration.

* * * * *

UNITED STATES PATENT AND TRADEMARK OFFICE
CERTIFICATE OF CORRECTION

Page 1 of 1

PATENT NO. : 10,752,664 B2
APPLICATION NO. : 14/009790
DATED : August 25, 2020
INVENTOR(S) : Xiong et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 500 days.

Signed and Sealed this
Seventh Day of February, 2023

Katherine Kelly Vidal
*Director of the United States Patent and Trademark Office*